(12) United States Patent
Klepper et al.

(10) Patent No.: US 8,142,530 B2
(45) Date of Patent: Mar. 27, 2012

(54) METHODS AND APPARATUS FOR PRODUCING SYNGAS AND ALCOHOLS

(75) Inventors: Robert E. Klepper, Arvada, CO (US); Arie Geertsema, Westminster, CO (US); Shakeel H. Tirmizi, Matawa, NJ (US); Heinz Juergen Robota, Arvada, CO (US); Francis M. Ferraro, Westminster, CO (US); Ronald C. Stites, Brighton, CO (US)

(73) Assignee: Range Fuels, Inc., Denver, CO (US)

( * ) Notice: Subject to any disclaimer, the term of this patent is extended or adjusted under 35 U.S.C. 154(b) by 935 days.

(21) Appl. No.: 12/166,183

(22) Filed: Jul. 1, 2008

(65) Prior Publication Data
US 2009/0018221 A1    Jan. 15, 2009

Related U.S. Application Data

(60) Provisional application No. 60/948,659, filed on Jul. 9, 2007.

(51) Int. Cl.
*C01B 3/36* (2006.01)
*C07C 31/08* (2006.01)
*C07C 31/10* (2006.01)
*C07C 31/12* (2006.01)
*C10J 3/46* (2006.01)

(52) U.S. Cl. ........ 48/197 R; 518/702; 518/703; 518/704

(58) Field of Classification Search ................ 48/197 R; 518/702, 703, 704
See application file for complete search history.

(56) References Cited

U.S. PATENT DOCUMENTS

| | | | |
|---|---|---|---|
| 4,171,461 A | 10/1979 | Bartish | |
| 4,233,466 A | 11/1980 | Fiato | |
| 4,253,987 A | 3/1981 | Fiato | |
| 4,277,634 A | 7/1981 | Walker | |
| 4,371,724 A | 2/1983 | Lin et al. | |
| 4,374,285 A | 2/1983 | Lin et al. | |
| 4,409,405 A | 10/1983 | Lin et al. | |
| 4,424,384 A | 1/1984 | Lin et al. | |
| 4,592,762 A | 6/1986 | Babu et al. | |
| 4,607,055 A | 8/1986 | Grazioso et al. | |
| 4,607,056 A | 8/1986 | Grazioso et al. | |
| 4,616,040 A | 10/1986 | Grazioso et al. | |
| 4,628,113 A | 12/1986 | Current | |

(Continued)

FOREIGN PATENT DOCUMENTS
EP    1860088    11/2007

(Continued)

OTHER PUBLICATIONS

Hironori Arakawa et al., "Selective Synthesis of Ethanol Over Rh-Ti-Fe-Ir/SiO2 Catalyst at High Pressure Syngas Conversion", Chemistry Letters, pp. 881-884, Mar. 11, 1985.

(Continued)

*Primary Examiner* — Timothy Vanoy
(74) *Attorney, Agent, or Firm* — O'Connor & Company; Ryan P. O'Connor

(57) ABSTRACT

This invention features methods and apparatus for producing syngas from any carbon-containing feed material. In some embodiments, a substoichiometric amount of oxygen is used to enhance the formation of syngas. In various embodiments, both oxygen and steam are added during the conversion of the feed material into syngas. The syngas can be converted to alcohols, such as ethanol, or to other products.

50 Claims, 9 Drawing Sheets

U.S. PATENT DOCUMENTS

| | | | |
|---|---|---|---|
| 4,661,525 | A | 4/1987 | Grazioso et al. |
| 4,675,344 | A | 6/1987 | Conway et al. |
| 4,699,632 | A | 10/1987 | Babu et al. |
| 4,749,724 | A | 6/1988 | Quarderer et al. |
| 4,752,622 | A | 6/1988 | Stevens |
| 4,752,623 | A | 6/1988 | Stevens |
| 4,762,858 | A | 8/1988 | Hucul et al. |
| 4,775,696 | A | 10/1988 | Prada-Silva et al. |
| 4,824,869 | A | 4/1989 | Prada-Silva et al. |
| 4,825,013 | A | 4/1989 | Quarderer et al. |
| 4,886,772 | A | 12/1989 | Prada-Silva et al. |
| 4,980,380 | A | 12/1990 | Wong et al. |
| 4,999,133 | A | 3/1991 | Banquy |
| 5,451,558 | A | 9/1995 | Campbell et al. |
| RE35,377 | E | 11/1996 | Steinberg et al. |
| 5,990,039 | A | 11/1999 | Paul et al. |
| 6,133,328 | A | 10/2000 | Lightner |
| 6,156,693 | A | 12/2000 | Song et al. |
| RE37,046 | E | 2/2001 | Hildinger et al. |
| 6,248,796 | B1 | 6/2001 | Jackson et al. |
| 6,281,158 | B1 | 8/2001 | Gabrielov et al. |
| 6,383,974 | B1 | 5/2002 | Ishida et al. |
| 6,387,842 | B1 | 5/2002 | Wegman et al. |
| 6,387,963 | B1 | 5/2002 | Fitzpatrick |
| 6,444,712 | B1 | 9/2002 | Janda |
| 6,451,729 | B1 | 9/2002 | Song et al. |
| 6,616,909 | B1 | 9/2003 | Tonkovich et al. |
| 6,641,625 | B1 | 11/2003 | Clawson et al. |
| 6,706,770 | B2 | 3/2004 | Patel et al. |
| 6,753,352 | B2 | 6/2004 | Seiki et al. |
| 6,753,353 | B2 | 6/2004 | Jackson et al. |
| 6,767,375 | B1 | 7/2004 | Pearson |
| 6,818,198 | B2 | 11/2004 | Singh et al. |
| 6,858,048 | B1 | 2/2005 | Jimeson et al. |
| 6,863,878 | B2 | 3/2005 | Klepper |
| 6,875,794 | B2 | 4/2005 | Seiki et al. |
| 6,894,080 | B2 | 5/2005 | Seiki et al. |
| 6,911,058 | B2 | 6/2005 | Calderon et al. |
| 6,919,488 | B2 | 7/2005 | Melnichuk et al. |
| 6,949,683 | B2 | 9/2005 | Wieland et al. |
| 6,981,994 | B2 | 1/2006 | Drnevich et al. |
| 6,991,769 | B2 | 1/2006 | Kaneko et al. |
| 7,008,967 | B2 | 3/2006 | Keyser et al. |
| 7,045,553 | B2 * | 5/2006 | Hershkowitz ............... 518/700 |
| 7,048,772 | B1 | 5/2006 | Bedetti |
| 7,091,251 | B2 | 8/2006 | Guillard et al. |
| 7,144,923 | B2 | 12/2006 | Fitzpatrick |
| 7,169,821 | B2 | 1/2007 | Branson |
| 7,176,160 | B2 | 2/2007 | Espinoza et al. |
| 7,192,987 | B2 | 3/2007 | Van Egmond et al. |
| 7,196,239 | B2 | 3/2007 | Van Egmond et al. |
| 7,214,721 | B2 | 5/2007 | Eastland |
| 7,279,019 | B2 | 10/2007 | Weedon |
| 7,638,070 | B2 | 12/2009 | Johnson et al. |
| 2006/0009537 | A1 | 1/2006 | Iordache-Cazana et al. |
| 2007/0004809 | A1 | 1/2007 | Lattner et al. |
| 2007/0205092 | A1 | 9/2007 | Klepper |

FOREIGN PATENT DOCUMENTS

| | | |
|---|---|---|
| EP | 1923380 | 5/2008 |
| JP | 2004-115365 A | 4/2004 |
| JP | 2004-339007 A | 12/2004 |

OTHER PUBLICATIONS

Division of Chemical Reaction Engineering, KTH—Kungl. Tekniska Högskolan, "Torrefied Wood an Alternative to Charcoal for Reducing Deforestation", http://hem.fyristorg.com/zanzi/torrefaction.html, Feb. 2001.

John L. Falconer et al., "Zeolite Membrane Research", http://www.colorado.edu/che/FalcGrp/research/zeolite.html (1996).

Jianli Hu et al., "Conversion of Biomass-Derived Syngas to Alcohols and C2 Oxygenates Using Supported Rh Catalysts in a Microchannel Reactor", Catalysis Today, vol. 120, pp. 90-95, Sep. 6, 2006.

Masaru Ichikawa et al., "Mechanism of Syngas Conversion Into C2-Oxygenates Such as Ethanol Catalysed on a SiO2-Supported Rh-Ti Catalyst", J. Chem. Soc., Chem. Commun., pp. 321-323 (1985).

Hongtao Ma et al., "Temperature-Programmed Surface Reaction Study on C2-Oxygenate Synthesis Over SiO2 and Nanoporous Zeolitic Material Supported Rh-Mn Catalysts", Surf. Interface Anal., vol. 32, pp. 224-227, Jan. 8, 2001.

C.B. Murchison et al., "Mixed Alcohols From Syngas Over Moly Catalysts", Proc. 9th Intern. Cong. Catal., vol. 2, pp. 626-633 (1988).

S. Phillips et al., "Thermochemical Ethanol via Indirect Gasification and Mixed Alcohol Synthesis of Lignocellulosic Biomass", NREL Technical Report/TP-510-41168 (Apr. 2007).

Jose G. Santiesteban et al., "Mechanism of C1-C4 Alcohol Synthesis Over Alkali/MoS2 and Alkali/Co/MoS2 Catalysts", Proc. 9th Intern. Cong. Catal., 2, 561-568 (1988).

P.L. Spath et al., Technical Report, "Preliminary Screening—Technical and Economic Assessment of Synthesis Gas to Fuels and Chemicals with Emphasis on the Potential for Biomass-Derived Syngas", NREL Report No. NREL/TP-510-34929, Dec. 2003.

G. Van Der Lee et al., "On the Selectivity of Rh Catalysts in the Formation of Oxygenates", Journal of Catalysis, vol. 98, pp. 522-529 (1986).

* cited by examiner

METHODS AND APPARATUS FOR PRODUCING SYNGAS AND ALCOHOLS

PRIORITY DATA

This patent application claims priority under 35 U.S.C. §120 from U.S. Provisional Patent Application No. 60/948,659 (filed Jul. 9, 2007) for "Methods and Apparatus for Producing Syngas and Alcohols" which is hereby incorporated by reference herein for all purposes.

FIELD OF THE INVENTION

The present invention generally relates to processes for the conversion of carbonaceous feedstocks, such as cellulosic biomass, into synthesis gas.

BACKGROUND OF THE INVENTION

Synthesis gas, which is also known as syngas, is a mixture of gases comprising carbon monoxide (CO) and hydrogen ($H_2$). Generally, syngas may be produced from any carbonaceous material. In particular, biomass such as agricultural wastes, forest products, grasses, and other cellulosic material may be converted to syngas.

Syngas is a platform intermediate in the chemical and biorefining industries and has a vast number of uses. Syngas can be converted into alkanes, olefins, oxygenates, and alcohols such as ethanol. These chemicals can be blended into, or used directly as, diesel fuel, gasoline, and other liquid fuels. Syngas can also be directly combusted to produce heat and power. The substitution of alcohols in place of petroleum-based fuels and fuel additives can be particularly environmentally friendly when the alcohols are produced from feed materials other than fossil fuels.

Improved methods and apparatus are needed to more cost-effectively produce syngas. Methods and apparatus are also desired for producing syngas at a greater purity and with desirable ratios of $H_2$ to CO to facilitate the conversion of syngas to other products, such as ethanol. Additionally, improved methods and apparatus to produce alcohols, such as ethanol, from syngas are needed commercially.

SUMMARY OF THE INVENTION

In one aspect of the present invention, a method is provided comprising the steps of:

(a) devolatilizing a carbon-containing feed material to form a gas phase and a solid phase in a devolatilization unit;

(b) passing the gas phase and the solid phase through a heated reaction vessel to form syngas;

(c) converting the syngas to a product, wherein step (a) is performed in the presence of free oxygen in an amount between about 0.1% and about 25% of the stoichiometric amount of oxygen to completely combust the feed material.

The product can be one or more of a variety of chemicals selected from alkanes, olefins, oxygenates, alcohols, and ethers. For example, the product can be selected from $C_1$ to $C_4$ alcohols. In some embodiments, the product is ethanol. In other embodiments, converting in step (c) comprises separation, and the product is purified hydrogen or purified carbon monoxide. The product can generally be any carbon-containing material, including purified solid carbon.

In some embodiments, step (b) is performed in the presence of free oxygen in an amount between about 0.1% and about 50% of the stoichiometric amount of oxygen to completely combust the carbon contained in the solid phase produced in step (a). The amount of free oxygen can be less than 10%, such as less than 1%, of the stoichiometric amount of oxygen to completely combust the feed material.

In some embodiments, step (a) is further performed in the presence of added steam. The added steam can be present in an amount that is less than about 50%, such as less than 10%, of the stoichiometric amount of water to completely convert the feed material to carbon monoxide and hydrogen. In certain embodiments, a first amount of steam is present from initial moisture in the carbon-containing feed material, a second amount of steam is added during step (a), and the combined first amount and second amount of steam is less than the stoichiometric amount of water to completely convert the feed material to carbon monoxide and hydrogen. In other embodiments, the combined first amount and second amount of steam is greater than such stoichiometric amount.

In variations where step (b) is performed in the presence of free oxygen in an amount between about 0.1% and about 50% (such as less than 25% or less than 10%) of the stoichiometric amount of oxygen to completely combust the carbon contained in the solid phase produced in step (a), step (b) can also be performed in the presence of steam. In some embodiments of these variations, an initial ratio of free oxygen to steam ($O_2/H_2O$) in step (b) is less than about 1, or less than 0.5, such as about 0.01-0.2.

In some embodiments, these methods further include the substeps of (i) measuring the composition of the gas phase and/or the solid phase, (ii) determining a suitable amount of free oxygen based on predicted partial oxidation of at least some of the composition to syngas, and (iii) introducing a gas containing the suitable amount of free oxygen.

The gas phase can optionally removed, at least in part, during step (a). For example, the devolatilization unit can be a multiple-stage unit in which both the gas phase and the solid phase pass through at least one stage of the devolatilization unit and at least a portion of the gas phase is removed from the devolatilization unit prior to a final stage. Prior to step (b), the solid phase can be recombined with gas removed during step (a).

In some embodiments, different amounts of oxygen can be added across stages of the devolatilization unit. Oxygen can be added to the devolatilization unit prior to removal of at least a portion of the gas phase. Or, after at least a portion of the gas phase is removed, oxygen can be added to the devolatilization unit. In some embodiments, a first amount of oxygen is added prior to removal of at least a portion of the gas phase, and a second amount of oxygen is added after removal of at least a portion of the gas phase. The first amount of oxygen can be less than, the same as, or greater than the second amount of oxygen.

In some preferred embodiments, the presence of free oxygen decreases the ratio of hydrogen to carbon monoxide in the syngas, compared to the ratio of hydrogen to carbon monoxide produced by the same method in the absence of oxygen. The presence of free oxygen can also preferably increase the amount of product produced compared to the amount of product produced by the same method in the absence of free oxygen.

In certain embodiments, the method includes introducing at least some of a stream produced in one or more steps selected from the group consisting of step (a), step (b), and step (c) to a reactor configured with an input for a gas comprising oxygen, wherein at least some of the stream is partially oxidized to produce additional syngas.

Step (c) as described above can, in certain embodiments of the invention, include the substeps of:

(i) introducing a first amount of syngas into a first reaction zone comprising at least a first catalyst;

(ii) converting at least a portion of the first amount of syngas to methanol with the first catalyst;

(iii) introducing the methanol to a second reaction zone comprising at least a second catalyst;

(iv) introducing a second amount of syngas to the second reaction zone; and (iv) reacting at least a portion of the methanol introduced into the second reaction zone with at least a portion of the second amount of syngas with the second catalyst to produce a product stream comprising ethanol.

The second amount of syngas can include syngas that did not react in the first reaction zone. The second amount of syngas can also include syngas that was separated and recycled from the product stream.

The first catalyst can comprise a material selected from the group consisting of $ZnO/Cr_2O_3$, $Cu/ZnO$, $Cu/ZnO/Al_2O_3$, $Cu/ZnO/Cr_2O_3$, $Cu/ThO_2$, Co/S, Mo/S, Co/Mo/S, Ni/S, Ni/Mo/S, Ni/Co/Mo/S, and any of the foregoing in combination with Mn and/or V. The first catalyst preferably includes a basic promoter.

The second catalyst can comprise a material selected from the group consisting of $ZnO/Cr_2O_3$, $Cu/ZnO$, $Cu/ZnO/Al_2O_3$, $CuO/CoO$, $CuO/CoO/Al_2O_3$, Co/S, Mo/S, Co/Mo/S, $Rh/Ti/SiO_2$, $Rh/Mn/SiO_2$, $Rh/Ti/Fe/Ir/SiO_2$, Rh/Mn/MCM-41, Ni/S, Ni/Mo/S, Ni/Co/Mo/S, and any of the foregoing in combination with Mn and/or V. The second catalyst preferably includes a basic promoter. The first and second catalysts can, in certain embodiments, have substantially the same composition.

In some embodiments, the first reaction zone is in a first reactor, the second reaction zone is in a second reactor, and an output stream of the first reactor comprises syngas introduced from the first reaction zone into the second reaction zone, further comprising separating from the output stream at least a portion of the methanol produced in the first reaction zone. Alternatively, the first reaction zone and second reaction zone can both be in a single reactor. As well, either or both of the reaction zones could actually include two or more reactors.

In some methods, additional or recycled $CO_2$ can be introduced into the first reaction zone, where at least a portion of the $CO_2$ is reacted with $H_2$ present to produce $CO_2$-derived methanol. The $CO_2$ can be produced during step (a) and/or step (b) and recycled into the first reaction zone.

Another aspect of the invention recognizes that syngas can be produced during devolatilization, which syngas can be used to produce a final product. This aspect provides a method of forming a product, the method comprising the steps of:

(a) devolatilizing a carbon-containing feed material to form a gas phase and a solid phase in a devolatilization unit, wherein the gas phase comprises syngas; and (b) converting the syngas to a product, wherein step (a) is performed in the presence of free oxygen in an amount between about 0.1% and about 25% of the stoichiometric amount of oxygen to completely combust the feed material.

The product can be selected from the group consisting of alkanes, olefins, oxygenates, alcohols, and ethers. The product can be selected from $C_1$ to $C_4$ alcohols, such as ethanol.

Figure 1:
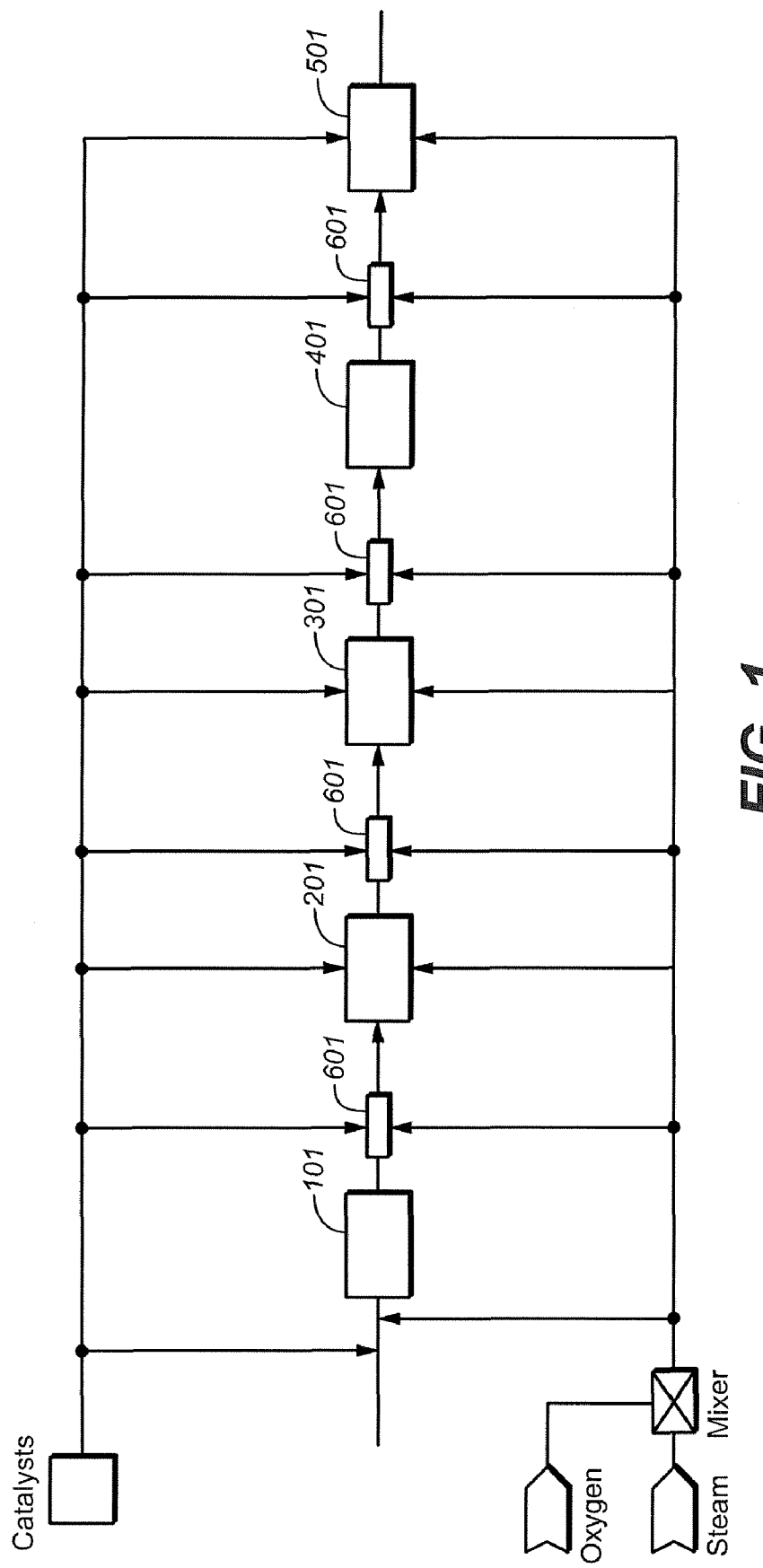
FIG. 1 shows a process flow for the production of syngas from any carbon-containing feed material, according to one variation.

These and other embodiments, features, and advantages of the present invention will become more apparent to those skilled in the art when taken with reference to the following detailed description of the invention in conjunction with the accompanying drawings.

DETAILED DESCRIPTION OF EMBODIMENTS OF THE INVENTION

Certain embodiments of the present invention will now be further described in more detail, in a manner that enables the claimed invention so that a person of ordinary skill in this art can make and use the present invention.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon the specific analytical technique. Any numerical value inherently contains certain errors necessarily resulting from the standard deviation found in its respective testing measurements.

All publications, patents, and patent applications cited in this specification are incorporated herein by reference in their entirety as if each publication, patent, or patent application was specifically and individually put forth herein.

The following detailed description should be read with reference to the drawings, in which identical reference numbers refer to like elements throughout the different figures. The drawings, which are not necessarily to scale, depict selected embodiments and are not intended to limit the scope of the invention. The detailed description illustrates by way of example, not by way of limitation, the principles of the invention.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. If a definition set forth in this section is contrary to or otherwise inconsistent with a definition set forth in patents, published patent applications, and other publications that are herein incorporated by reference, the definition set forth in this specification prevails over the definition that is incorporated herein by reference.

The present invention provides methods and apparatus for producing syngas from any carbon-containing feed material. The present invention is premised, at least in part, on the addition of a substoichiometric amount of oxygen during the conversion of a carbon-containing feed material to syngas.

In some embodiments, oxygen is mixed with steam, and the resulting mixture is added to the system for generating syngas. In contrast to some prior methods that conducted the devolatilization and reforming process for the production of syngas within a controlled reducing environment, the present invention employs the concept that oxygen or oxygen-enriched air can be added to the system (i) to supply an enthalpy source that displaces additional fuel requirements, e.g. by causing an exothermic reaction such as the partial or total oxidation of carbon or devolatilization products with oxygen; (ii) to achieve a more favorable $H_2/CO$ ratio in the syngas, which can increase the yield of products formed from the syngas; (iii) to increase the yield of syngas, e.g. by reducing the formation of less-reactive compounds and/or by converting certain species to syngas; and/or (iv) to increase the purity of syngas, e.g. by reducing the amount of $CO_2$, pyrolysis products, tar, aromatic compounds, and/or other undesirable products.

All references herein to a "ratio" of chemical species are references to molar ratios unless otherwise indicated. For example, a $H_2/CO$ ratio of 1 means one mole of hydrogen per mole of carbon dioxide; an $O_2/H_2O$ ratio of 0.1 means one mole of molecular oxygen per ten moles of water.

By "free oxygen," as used herein, it is meant oxygen that is contained solely in the gas phase. Free oxygen does not include the oxygen content of the biomass itself or of any other solid or liquid phase present, and does not include oxygen that is physically adsorbed onto a surface. Generally, "gas phase" refers to the vapor phase under the particular process conditions, and will include components that are condensable at other conditions (such as lower temperature).

By "added steam" as used herein, it is meant steam (i.e. $H_2O$ in a vapor phase) that is introduced into a system or apparatus in one or more input streams. Added steam does not include (i) steam generated by moisture contained in the solid biomass or in another material present, (ii) steam generated by vaporization of water that may have initially been present in the system or apparatus, or (iii) steam generated by any chemical reactions that produce water.

Steam reforming, partial oxidation, water-gas shift (WGS), and/or combustion reactions can occur when oxygen or steam are added. Exemplary reactions are shown below with respect to a cellulose repeat unit ($C_6H_{10}O_5$) found, for example, in cellulosic feedstocks. Similar reactions can occur with any carbon-containing feedstock.

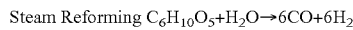
Steam Reforming $C_6H_{10}O_5 + H_2O \rightarrow 6CO + 6H_2$

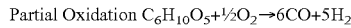
Partial Oxidation $C_6H_{10}O_5 + \frac{1}{2}O_2 \rightarrow 6CO + 5H_2$

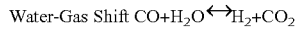
Water-Gas Shift $CO + H_2O \leftrightarrow H_2 + CO_2$

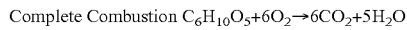
Complete Combustion $C_6H_{10}O_5 + 6O_2 \rightarrow 6CO_2 + 5H_2O$

FIG. 1 illustrates an exemplary process for synthesizing syngas from biomass or another carbon-containing material. The feed material is introduced into a devolatilization unit 201 through a feed section 101. The product that exits the devolatilization unit 201 comprises a gas phase and a solid phase and can further include one or more liquid phases. A stream exiting the devolatilization unit 201 is introduced into a heated reaction vessel 301, which in FIG. 1 is shown as a reformer reactor, where additional syngas is produced. The syngas produced in the reformer reactor 301 is introduced into a quench and compressing section 401, where the syngas is cooled and compressed.

The "heated reaction vessel" 301 is any reactor capable of causing at least one chemical reaction that produces syngas. Conventional steam reformers, well-known in the art, can be used either with or without a catalyst. Other possibilities include autothermal reformers, partial-oxidation reactors, and multistaged reactors that combine several reaction mechanisms (e.g., partial oxidation followed by water-gas shift). The reactor 301 configuration can be a fixed bed, a fluidized bed, a plurality of microchannels, or some other configuration. As will be further described below, heat can be supplied to reactor 301 in many ways including, for example, by oxidation reactions resulting from oxygen added to the process.

In some variations, the syngas from the devolatilization unit 201 and/or the heated reaction vessel 301 is filtered, purified, or otherwise conditioned prior to being converted to another product. For example, the cooled and compressed syngas may be introduced to a syngas conditioning section 501, where benzene, toluene, ethyl benzene, xylene, sulfur compounds, nitrogen, metals, and/or other impurities or potential catalyst poisons are optionally removed from the syngas. If desired, burners 601 can be used to heat the catalyst, oxygen, and/or steam that are added.

Oxygen can assist pyrolysis and/or cracking reactions in the devolatilization unit 201 and/or generate heat (which can provide a temperature rise) from partial oxidation. As illustrated in FIG. 1, oxygen or a mixture of oxygen and steam can be added at any stage of the process for producing syngas. For example, oxygen may be added directly to the feed material, to the feed section 101, before or while the feed material enters the devolatilization unit 201, directly into the devolatilization unit 201, before the exhaust gas/solids from the devolatilization unit 201 enter the reformer reactor 301, directly into the reformer reactor 301 (such as into the cold chambers 302 and/or hot chambers 304 of the reformer reactor 301 shown in FIG. 4), before the syngas product from the reformer reactor 301 enter the quench and compressing section 401, before the syngas enters the conditioning section 501, directly into the syngas conditioning section 501, and/or to one or more various recycle streams. In some embodiments, oxygen or a mixture of oxygen and steam are added at multiple locations.

In some embodiments, a substoichiometric amount of oxygen is added. A "stoichiometric amount of oxygen" is calculated based on the amount of oxygen that would be required to completely combust the feed material (entering feed section 101) into $CO_2$ and $H_2O$; this calculation is independent of the amount of steam that is added or the location(s) of oxygen addition. In some embodiments, the total amount of the oxygen added (e.g., the sum of the amounts of oxygen added at one or more locations in the system) or the amount of oxygen present at any point during the process is between about 0.1% and about 75% of the stoichiometric amount of oxygen for combustion. In embodiments, the amount of oxygen is less than about any of 75%, 50%, 25%, 10%, 5%, 2%, 1%, 0.5%, or 0.1% of the stoichiometric amount of oxygen.

In certain embodiments, the amount of oxygen is between about 1-25%, preferably between about 2-20%, and more preferably between about 5-10% of the oxygen required to completely combust the feed material. In other embodiments, the amount of oxygen is between about 0.1-10%, preferably between about 0.1-1%, and more preferably between about 0.1-0.5% of the oxygen required to completely combust the feed material.

In some embodiments, the amount of oxygen added specifically to the devolatilization unit 201 is less than about any of 1%, 0.5%, or 0.1% of the stoichiometric amount of oxygen. In some embodiments, the amount of oxygen added to the reformer reactor 301 is less than about any of 25%, 10%, 5%, 2%, 1%, 0.5%, or 0.1% of the stoichiometric amount of oxygen. In embodiments wherein oxygen is added to the reformer reactor 301 to generate heat from exothermic partial oxidation, the amount of oxygen added to the reformer reactor 301 can be about 1% to about 10% (such as about 5%) of the stoichiometric amount of oxygen. In embodiments wherein oxygen is added to the reformer reactor 301 to generate a lower ratio of $H_2/CO$ in the syngas than would be generated in the absence of oxygen, the amount of oxygen added to the reformer reactor 301 can be about 10% to about 50% (such as about 25%) of the stoichiometric amount of oxygen.

It will be appreciated by a skilled artisan that in carrying out these methods, the amount of oxygen to be added to the process can be calculated or estimated in a number of ways other than by determining overall feedstock composition. For example, one can measure the carbon content of a feed material and base the amount of oxygen on some fraction of that which would be predicted to completely convert the carbon to $CO_2$. Similarly, a feedstock heating value can be determined and an amount of oxygen to be added can be determined. Alternatively, or additionally, one can measure the composition, carbon content, or heating value of an intermediate stream or streams into which oxygen can be added. The substoichiometric amounts of oxygen recited herein use a basis of complete combustion for convenience only and do not limit the scope of the invention in any way.

Oxygen and/or steam can be present for a portion of or for the entire time the feed material passes through the devolatilization unit 201 and/or reformer reactor 301. In some embodiments, a separate partial-oxidation reactor (not shown) is added between the devolatilization unit 201 and the reformer reactor 301 or added downstream of the reformer reactor 301 (such as between the reformer reactor 301 and the quench and compressing section 401).

Another variation of the invention is premised on the realization that during devolatilization, such as in the devolatilization unit 201 (or another suitable devolatilization reactor or vessel), the gas phase so generated contains at least some syngas. The amount and quality of syngas produced during this step may be adjusted by oxygen and/or steam addition, in amounts as described herein, as well as by temperature, pressure, and other conditions. The syngas from devolatilization can be of sufficient quality for some applications. Therefore, in some embodiments, a gas phase and solid phase from devolatilization need not proceed to a separate heated reaction vessel (such as a steam reformer). Instead, the gas and solid phases may be collected and used directly; or, one or both of these phases may be stored for future use.

In some embodiments of the invention, the total amount of steam added (e.g., the sum of the amounts of steam added at one or more locations in the system) or the amount of steam present at any point during the process is at least about 0.1 mole of steam per mole of carbon in the feed material. In various embodiments, at least about any of 0.5, 1.0, 1.5, 2.0, 3.0, 4.0, 5.0, or more moles of steam are added or are present per mole of carbon. In some embodiments, between about 1.5-3.0 moles of steam are added or are present per mole carbon.

The amount to steam that is added to the heated reaction vessel 301 can vary depending on factors such as the performance in the devolatilization unit 201. When devolatilization produces a carbon-rich solid material, generally more steam (and/or more oxygen) is used to add the necessary H and O atoms to the C available to generate CO and $H_2$. From the perspective of the overall system, the moisture contained in the feed material can be accounted for in determining how much additional water (steam) to add in the process.

Steam is generally used to steam reform, inside the reformer reactor 301, gases and/or solids exiting the devolatilization unit 201. In some embodiments, steam is used, in part, to push feed material through the devolatilization unit 201. In certain embodiments, more steam is added to the reformer reactor 301 than to the devolatilization unit 201.

In some embodiments, the humidity of the gas produced from the feed material is measured at any point in the process and an appropriate amount of steam is added to maintain a desired humidity level. For example, gas from the devolatilization unit 201 can be analyzed to determine the amount of steam present and then more steam can be added, if desired.

Exemplary ratios of oxygen added to steam added ($O_2/H_2O$) are equal to or less than about any of 2, 1.5, 1, 0.5, 0.2, 0.1, 0.05, 0.02, 0.01, or less. Exemplary ratios of oxygen added to steam present, which includes $H_2O$ from moisture that was present prior to the addition of steam, any $H_2O$ generated by chemical reactions, and $H_2O$ from the addition of steam, are equal to or less than about any of 1, 0.5, 0.4, 0.3, 0.2, 0.1, 0.05, 0.04, 0.03, 0.02, 0.01, or less. Exemplary ratios of oxygen added to steam added or present are between about 0.01-2, between about 0.02-0.5, or between about 0.05-0.2. When the ratio of $O_2/H_2O$ is greater than 1, the combustion reaction starts to dominate over partial oxidation, which may produce undesirably low $CO/CO_2$ ratios.

In some embodiments, oxygen without steam is added at one or more locations in the system. In some embodiments, steam without oxygen is added at one or more locations in the system. In various embodiments, oxygen without steam is added at one or more locations in the system, and steam without oxygen is added at one or more different locations. A mixture of oxygen and steam can be added at one or more locations in the system. In certain embodiments, oxygen without steam is added at one location, steam without oxygen is added at another location, and a mixture of oxygen and steam is added at yet another location. In some embodiments, a mixture of oxygen and steam is added at different $O_2/H_2O$ ratios in two or more locations.

In particular embodiments, steam is added to the devolatilization unit 201, while oxygen is not added to the devolatilization unit 201. In particular embodiments, both oxygen and steam are added to the reformer reactor 301. In some embodiments, oxygen but not steam is fed to a partial-oxidation reactor that is in communication with the devolatilization unit 201 and/or reformer reactor 301.

Oxygen and steam can be added to the system as one stream, or steam and oxygen can be injected as separate streams into the same or different locations. In some embodiments, steam and oxygen are added in a manner that creates a reasonably uniform reaction zone to avoid localized zones of different stoichiometries in a reactor or other vessel. In some embodiments, oxygen and steam are added in different locations such that partial oxidation and steam reforming initially occur in different locations, with the resulting components being later combined such that a combination of partial oxidation and steam reforming can occur effectively in a single location.

Oxygen can be added in substantially pure form, or it can be fed to the process through the addition of air, optionally enriched with oxygen. In some embodiments, air that is not enriched for oxygen is added. In other embodiments, enriched air from an off-spec or recycle stream, which may be a stream from a nearby air-separation plant, for example, can be used. In some embodiments, the use of enriched air with a reduced amount of $N_2$ (i.e., less than 79 vol %) results in less $N_2$ in the resulting syngas. Because removal of $N_2$ can be expensive, methods of producing syngas with less or no $N_2$ are typically desirable, when the syngas is intended for synthesis of liquid fuels such as alcohols.

In some embodiments, the presence of oxygen alters the ratio of $H_2/CO$ in the syngas, compared to the ratio produced by the same method in the absence of oxygen. The $H_2/CO$ ratio of the syngas can be between about 0.5 to about 2.0, such as between about 0.75-1.25, about 1-1.5, or about 1.5-2.0. As will be recognized, increased water-gas shift (by higher rates of steam addition) will tend to produce higher $H_2/CO$ ratios, such as at least 2.0, 3.0. 4.0. 5.0, or even higher, which may be desired for certain applications. When low $H_2/CO$ ratios are desired in the syngas stream, it can be advantageous to decrease steam addition and increase oxygen addition, as described in various embodiments herein.

The $H_2/CO$ ratio in the syngas can affect the yield of downstream products such as methanol or ethanol. The preferred $H_2/CO$ ratio may depend on the catalyst(s) used to produce the desired product (from syngas) as well as on the operating conditions. Consequently, in some variations the production and/or subsequent conditioning of syngas is controlled to produce syngas having a $H_2/CO$ ratio within a range desired to optimize, for example, production of methanol, ethanol, or both methanol and ethanol.

In some variations, the $H_2/CO$ ratio of the syngas produced using the methods described herein can provide an increased product (e.g., $C_2$-$C_4$ alcohols) yield compared to that which would be provided by syngas produced by the corresponding methods in the absence of oxygen. This effect can be caused, for example, by faster kinetic rates toward desired products at reduced $H_2/CO$ ratios; e.g., the rate of ethanol formation can be faster for $H_2/CO$=1-1.5 compared to $H_2/CO$=1.5-2, for certain catalysts and conditions.

Some embodiments of the invention provide methods of controlling the $H_2/CO$ ratio of the syngas by adjusting the amount and/or location of oxygen addition dynamically during the process. It can be advantageous to monitor the $H_2/CO$ ratio of the syngas in substantially real-time, and adjust the amount and/or location of $O_2$ addition to keep the $H_2/CO$ ratio at (or near) a prescribed level. Also, it can be beneficial to change the $H_2/CO$ ratio in response to some variation in the process (e.g., feedstock composition changes) or variation in conditions (e.g., catalyst deactivation), for better overall performance.

Catalysts that facilitate the devolatilization, reforming, and/or partial-oxidation reactions can optionally be provided at any stage of the process for producing syngas. Referring again to FIG. 1, one or more catalysts may be added directly to the feed material, to the feed section 101, before or while the feed material enters the devolatilization unit 201, directly into the devolatilization unit 201, before the exhaust gas/solids from the devolatilization unit 210 enter the reformer reactor 301, directly into the reformer reactor 301 (e.g., addition of reforming and/or partial-oxidation catalysts can be added to the cold 302 and/or hot chambers 304 of the reformer reactor shown in FIG. 4) before the syngas product from the reformer reactor 301 enters the quench and compressing section 401, before the syngas enters the conditioning section 501, directly into the syngas conditioning section 501, and/or added to recycle streams. In some embodiments, one or more catalysts are added at multiple locations. In some embodiments, a catalyst is added at the same location where oxygen or a mixture of oxygen and steam are added.

Catalysts used for devolatilization include, but are not limited to, alkali metal salts, alkaline earth metal oxides and salts, mineral substances or ash in coal, transition metals and their oxides and salts, and eutectic salt mixtures. Specific examples of catalysts include, but are not limited to, potassium hydroxide, potassium carbonate, lithium hydroxide, lithium carbonate, cesium hydroxide, nickel oxide, nickel-substituted synthetic mica montmorillonite (NiSMM), NiSMM-supported molybdenum, iron hydroxyoxide, iron nitrate, iron-calcium-impregnated salts, nickel uranyl oxide, sodium fluoride, and cryolite. Devolatilization catalysis includes catalysis of devolatilization or gasification per se, as well as catalysis of tar cracking reactions or pyrolysis. In some embodiments, the devolatilization catalyst is between about 1 to about 100 μm in size, such as about 10-50 μm. Other sizes of catalyst particles are, however, possible.

Reforming and/or partial-oxidation catalysts include, but are not limited to, nickel, nickel oxide, rhodium, ruthenium, iridium, palladium, and platinum. Such catalysts can be coated or deposited onto one or more support materials, such as, for example, gamma-alumina (optionally doped with a stabilizing element such as magnesium, lanthanum, or barium). In some embodiments, the reforming and/or partial-oxidation catalyst is between about 1 to about 1000 nm in size, such as about 10-100 nm. Other catalyst sizes are, however, possible.

Before being added to the system, any catalyst can be pretreated or activated using known techniques that impact total surface area, active surface area, site density, catalyst stability, catalyst lifetime, catalyst composition, surface roughness, surface dispersion, porosity, density, and/or thermal diffusivity. Pretreatments of catalysts include, but are not limited to, calcining, washcoat addition, particle-size reduction, and surface activation by thermal or chemical means.

Catalyst addition can be performed by first dissolving or slurrying the catalyst(s) into a solvent such as water or any hydrocarbon that can be gasified and/or reformed. Examples of hydrocarbon solvents include acetone, ethanol, or mixtures of alcohols. In some embodiments, the catalyst is added by direct injection of such a slurry into a vessel (e.g., using high-pressure pumps such as common HPLC pumps or syringe pumps). In some embodiments, the catalyst is added to steam and the steam/catalyst mixture is added to the system. In these embodiments, the added catalyst may be at or near its equilibrium solubility in the steam or may be introduced as particles entrained in the steam and thereby introduced into the system.

In some embodiments, catalysts are introduced indirectly. For example, catalysis may occur due to impurities present in the feed material, from recycle streams, or from materials of construction. These indirect catalysts may or may not be beneficial. Preferably, but not necessarily, these catalyst sources are identified and monitored in overall process control and operation.

Catalysts can optionally be recovered from certain intermediate or byproduct streams, such as ash from the ash-quench/slag-removal system 520 (FIG. 5), using methods known in the art.

The methods and systems of the invention can accommodate a wide range of feedstocks of various types, sizes, and moisture contents. Any carbon-containing compound can be used as a feed material for the production of syngas. For example, biomass such as agricultural wastes, forest products, grasses, and other cellulosic material can be used. In some embodiments, the feedstock includes one or more materials selected from timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. A person of ordinary skill in the art will appreciate that the feedstock options are virtually unlimited.

Referring to FIG. 1, the feed section 101 of FIG. 1 can include a feed distribution system, a charging hopper, and a lock hopper (not shown), for example. In some embodiments, multiple charging hoppers and lock hoppers are used. Feed material (such as wood chips) is received from the distribution system into the charging hopper. Each charging hopper feeds a lock hopper that, in turn, feeds material such as wood chips to two devolatilization stacks (701 in FIG. 2B) contained in the devolatilization unit 201.

In some embodiments, the system processes about 1 to about 5,000 dry tons per day ("DTPD") of various timber and other biomass feed materials for conversion to syngas, which is suitable for conversion into fuel-quality alcohols such as ethanol.

In some embodiments, the feedstock substantially consists of southern pine that has been chipped to a characteristic length scale of about one inch. An exemplary composition of southern pine, on a dry basis, is 56 wt % carbon, 5.4 wt % hydrogen, 37 wt % oxygen, 0.4 wt % nitrogen, 0.7 wt % ash, and trace amounts of sulfur. Moisture levels of the feed material can vary widely, depending on harvest and storage condition, and can range from about 10% to about 60%.

In some embodiments, the feed material is torrefied biomass such as torrefied wood. Torrefaction consists of a slow heating of biomass in an inert atmosphere to a maximum temperature of about 300° C. The treatment yields a solid uniform product with a lower moisture content and a higher energy content compared to the initial biomass. Torrefied biomass is hydrophobic—it does not regain humidity in storage and therefore is relatively stable—and will generally have a lower moisture content and higher energy value compared to the initial biomass. In some embodiments, a feed material is torrefied before it is added to devolatilization unit 201. In other embodiments, torrefaction occurs, to some extent, within devolatilization unit 201.

Figure 2A:
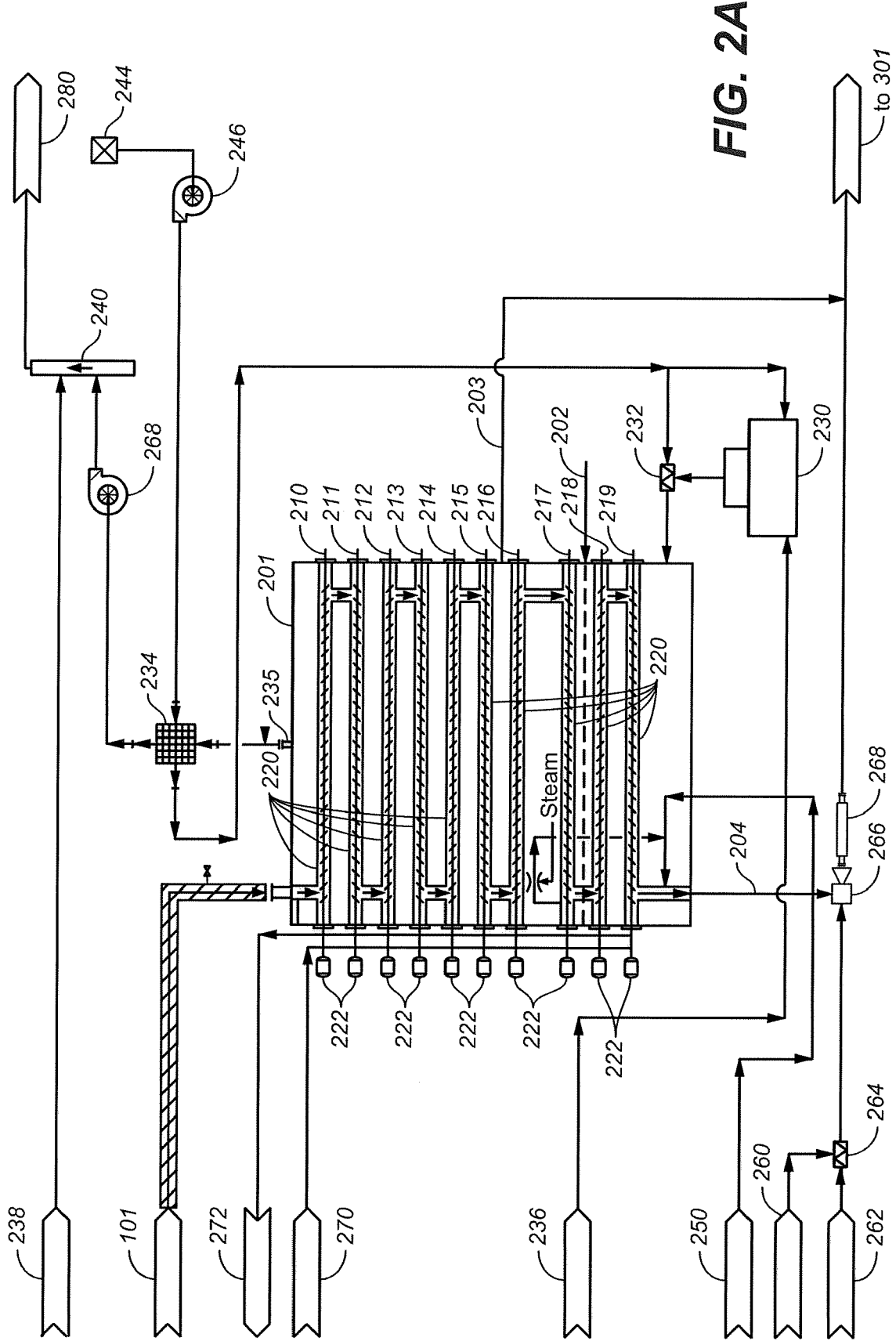
FIG. 2A shows a process flow for a two-stage devolatilization unit, according to one variation.

FIG. 2A depicts a devolatilization unit 201 that is connected to the lock hopper (not shown) from the feed section 101. The reaction product exiting from the devolatilization unit 201 is introduced to a reformer reactor 301, according to the embodiments depicted in these drawings. When feed material such as wood chips is conveyed through the devolatilization unit 201, it can undergo torrefaction, gasification, and/or devolatilization. These processes reduce the mass and volume of the conveyed solids, with a corresponding increase in the mass and volume of volatilized gas.

Figure 2B:
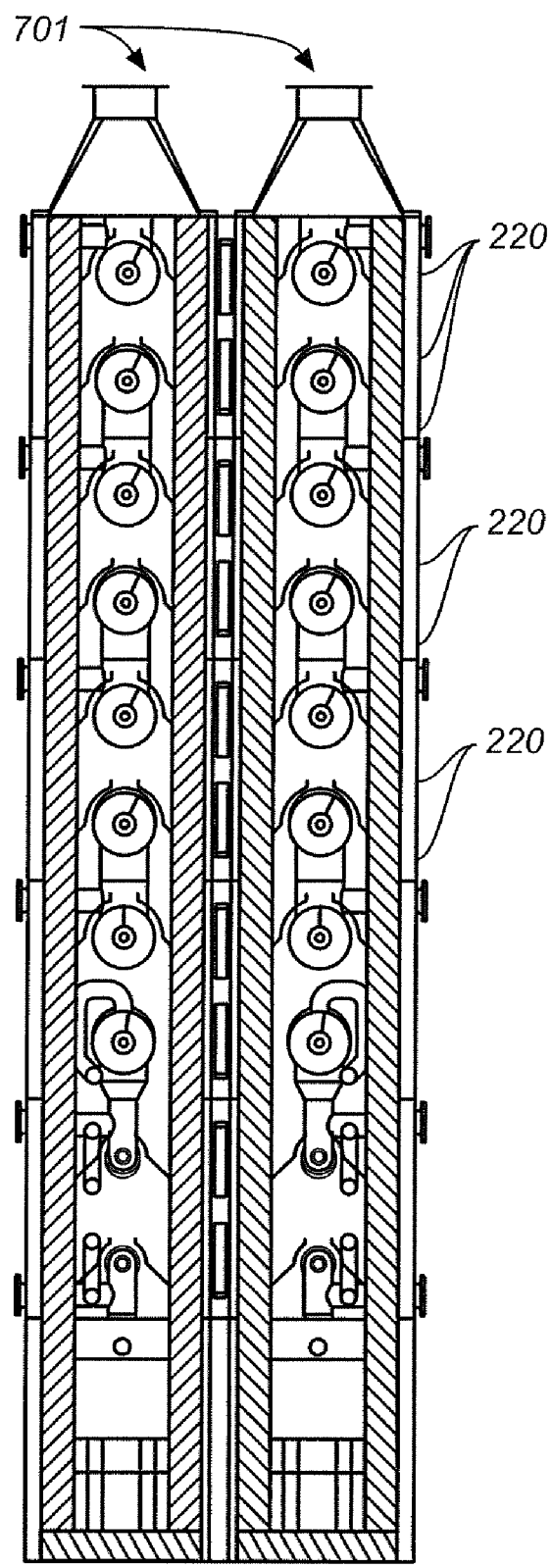
FIG. 2B shows a side view of the two-stage devolatilization unit shown in FIG. 2A, according to one variation.

As illustrated in FIGS. 2A and 2B, which depict the front and side view of devolatilization unit 201, respectively, the devolatilization unit 201 consists of two devolatilization stacks 701, positioned next to each other. Each stack 701 includes a series of reaction chambers 210-219. Each chamber is in connection with the next chamber. Each chamber includes one auger 220. The augers and down-corner pipes distribute feed material into each devolatilization chamber 210-219 and convey the feed material flow in each devolatilization chamber 210-219 horizontally. An exemplary down-corner pipe is the section shown in FIG. 2A connecting chambers 210 and 211. The augers 220 are operated by motors 222. A cooling-water supply that is used to cool down the motor temperature has an inlet 270 and an outlet 272. In some embodiments, motors 222 can be variable frequency drives that are equipped with torque sensors at each end of the auger with speed control.

In some embodiments, one or more of the augers 220 are twin screws, such as a pair of overlapping or intermeshing screws mounted (e.g., a pair of screws at the same elevation or a pair of screws at different elevations) that are used to move the feed material through the devolatilization unit 201. The twin screws are preferably designed to ensure efficient movement of feed material forward, minimize the possibility of backward flow of material, ensure a substantially uniform temperature distribution in the radial direction, and/or prevent release of materials, thereby allowing safe operation and a good operating lifetime.

Other means of conveying material through the devolatilization unit 201 are certainly possible and within the scope of the present invention. Material can generally be conveyed by single screws, twin screws, rams, and the like. Material can be conveyed mechanically through the devolatilization unit 201 by physical force (metal contact), pressure-driven flow, pneumatically driven flow, centrifugal flow, gravitational flow, fluidized flow, or some other known means of moving solid and gas phases.

In some embodiments, the temperature within the devolatilization unit 201 increases as the feed material progresses through the devolatilization unit 201. In some embodiments, the feed material enters devolatilization unit 201 at about ambient temperature and exits the devolatilization unit 201 between about 450-1000° F. (such as between 900-1000° F.). In some embodiments in which devolatilization is performed in the presence of oxygen, the temperature increases due to the exothermic partial oxidization of material in the devolatilization unit 201. In various embodiments, the pressure is between about 50 to about 200 psig, such as about 100-150 psig. Feed material is conveyed inside the tubes in the cascading auger system and is heated in the enclosed auger system. A bypass gas line can recombine recycled unreacted product gas from a high-pressure separator 250 and the process stream and run it back through the devolatilization unit 201.

Heat is supplied to the devolatilization unit 201 by a set of burners 230, which are connected to the devolatilization unit 201 through a set of air mixers 232. Heat can be supplied in two different modes: start-up and normal operation. A common burner system can be utilized for both modes. At start-up heating mode, natural gas 236 is combusted and the flue gas is used as the hot process stream for the devolatilization unit 201. During normal operation, the combustion fuel is unreacted product gas, optionally supplemented with natural gas. In some embodiments, the devolatilization burners are also fueled with syngas produced by the reformer reactors 301. As syngas is produced, more syngas and less natural gas can be preferably used to heat the devolatilization unit 201.

Devolatilization outlet 235 directs devolatilization flue gas into a devolatilization combustion-air preheater 234, where the devolatilization flue gas is cooled and exchanges enthalpy with devolatilization combustion air 244, which is introduced into the air preheater 234 through a devolatilization combustion air blower 246. The preheated air is split as feed introduced to the burners 230, as well as feed introduced directly to the air mixers 232. The preheated air is introduced to the air mixers 232 to combine with burner flue gases from the burners 230 to help maintain the devolatilization inlet air temperature.

The devolatilization combustion air preheater 234 also directs partial preheated air into a devolatilization induced draft fan 248, which can communicate with a stack 240, where the preheated air is joined with reformer flue gas 238 that exits from the reformer reactor 301. The flue gas exiting from the stack 240 exits the system through an exhaust line 280 and through subsequent heat-exchange equipment (not shown).

The devolatilization unit can be a single-stage unit or can optionally be divided into multiple stages. For present purposes, a "stage" is a physical zone within the unit, and does not relate to temporal considerations. Also, the number of stages is independent of the number of actual augers, downcorner pipes, stacks, or other physical implementation. Specification and delineation of stages can be done for any purpose, such as for temperature control, measurement points, residence-time distribution, or for the presence of various input or output streams.

A multiple-stage devolatilization unit can generally be desirable for certain feed materials for which it would be beneficial to remove some or all of the devolatilized gas prior to the end of the devolatilization unit 201. For example, rapid removal of devolatilized gas can help prevent undesirable gas-phase chemistry, such as polymerization leading to tar formation. When syngas is the desired product and devolatilization produces at least some syngas, it can be desirable to remove syngas upon generation rather than allowing it to possibly react with other components present. Also, it can be more energy-efficient to process the gas phase 203 for a shorter amount of time than the solid phase 204 in the devolatilization unit 201. "Multiple stages" can mean 2, 3, 4, 5, or more stages of devolatilization.

FIG. 2A depicts a two-stage devolatilization unit 201 such that the gas phase 203 and solid phase 204 exit the devolatilization unit 201 at different places. The optional passage of the solid phase 204 through a second portion of the devolatilization unit 201 that the gas phase 203 is not passed through allows the solid phase 204 to be treated for longer in the devolatilization unit 201.

As shown in FIG. 2A, the gas phase 203 of the devolatilization product leaves the devolatilization unit 201 and exits from one or more top stage(s). The solid phase 204 of the devolatilization product stays in the devolatilization unit 201 longer and exits from the bottom stage. A two-stage devolatilization unit 201 is shown in FIG. 2A wherein the top stage and the bottom stage are divided by a dashed line 202. The gas/solid separation can occur, for example, in a cyclone device that separates the gas phase from the solid phase primarily by density difference.

In some embodiments, the solid phase 204 and the gas phase 203 enter the reformer separately, and a different amount of oxygen and/or steam is added to the solid phase 204 compared to the amount added to the gas phase 203 of the material leaving the devolatilization unit 201. For example, the compositions of the solid phase 204 and gas phase 203 leaving the devolatilization unit 201 can be measured or estimated, and the amount of oxygen and/or steam that is added to each phase can be determined based on the composition of each phase (such as the amount of carbon in each phase). In some embodiments, less oxygen and/or steam is added to the gas phase 202 than the solid phase 204. In some embodiments, steam is added to the gas phase 203 to enrich it towards hydrogen by the water-gas shift reaction.

In some embodiments, steam 262 is used to obtain the desired $H_2/CO$ ratio of syngas from the reformer reactor 301. The oxygen 260 can partially oxidize the devolatilization product and boost the process temperature prior to feeding to the reformer in order to lower the reformer burner heat duty. In some preferred embodiments, oxygen feed 260 (or air feed) and superheated steam feed 262 are mixed in a reformer feed steam/oxygen mixer 264 and then introduced into an eductor 266, where the solid phase 204 of the devolatilization product from the devolatilization unit 201 joins the oxygen/steam stream. The mixture is then introduced into the reformer reactor 301.

In some embodiments, the gas phase 203 of the devolatilization product from the devolatilization unit 201 is combined with the solid phase 204 and the mixture is then introduced to the eductor 266 and the burner 268. In some other embodiments, the gas phase 203 can be introduced into the reformer reactor 301 directly. In some embodiments, the gas phase 203 is combined with oxygen and/or steam before it is introduced into the reformer reactor 301 directly. Steam flow to the eductor 266 can be controlled, for example, by monitoring concentrations of CO, $H_2$, or both. Oxygen 260 to the eductor 266 can be controlled, for example, by the temperature downstream of the eductor 266 and/or the temperature at the reformer reactor 301 inlet.

In one embodiment, reformer feed steam/oxygen mixers 264 combine oxygen and steam (which steam can be superheated) and introduce the mixture of steam and oxygen to the eductor 266. The remaining solids from the devolatilization unit 201 are entrained in the gaseous volatilized products to the entrance of reformer reactor 301. In some embodiments when oxygen is not added prior to the reformer reactor 301, a burner can be used to heat the products from the devolatilization unit 201 before they enter the reformer reactor 301. When oxygen is added prior to the reformer reactor 301, a burner can be unnecessary to heat the products from the devolatilization unit 201 before they enter the reformer reactor 301, due to the heat generated by exothermic partial oxidation.

Figure 3:
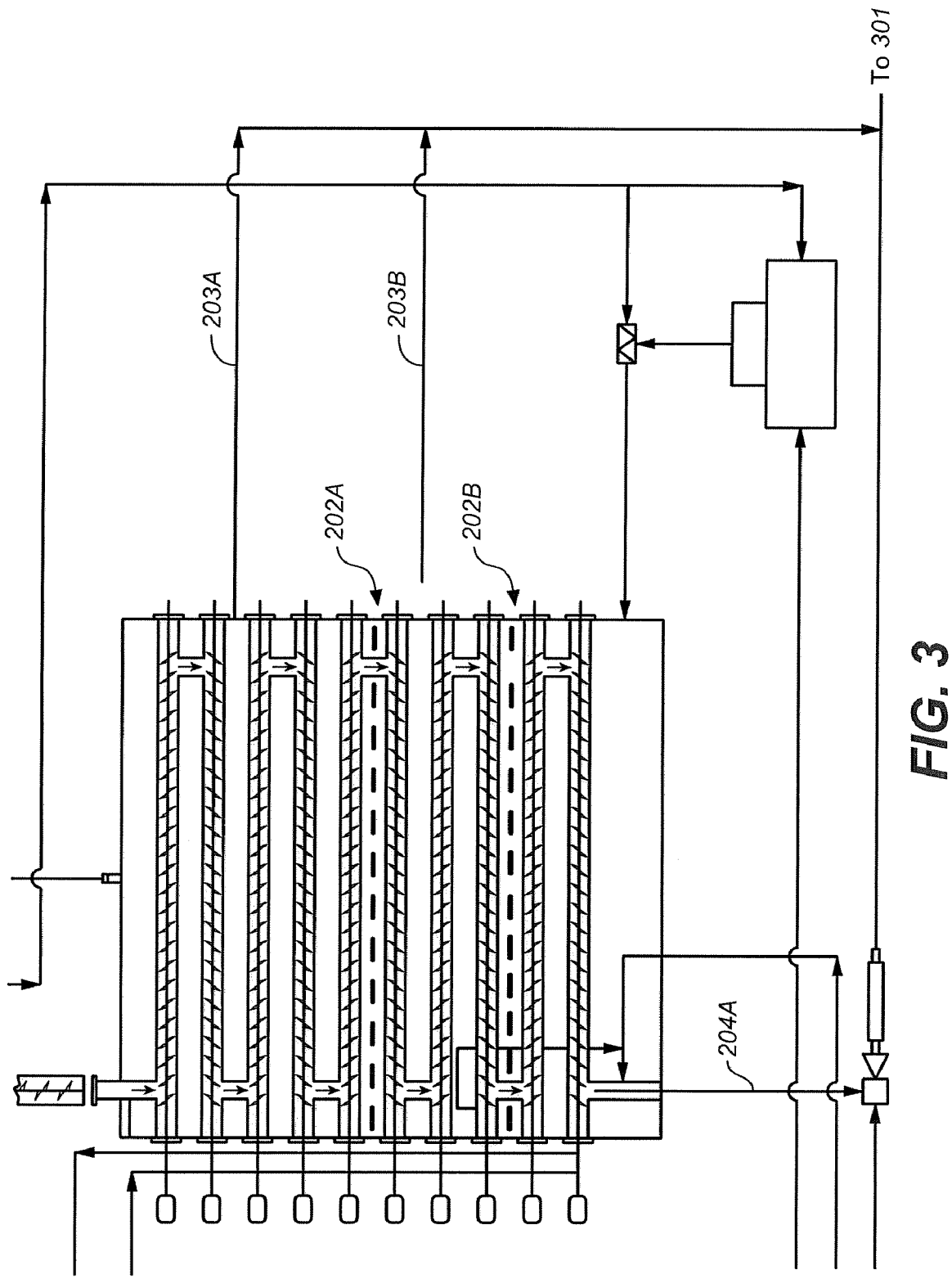
FIG. 3 shows a process flow for a three-stage devolatilization unit, according to one variation.

FIG. 3 depicts a three-stage devolatilization unit. The top two stages and the bottom stage are divided by dashed lines 202A and 202B. The gas phases 203A and 203B of the devolatilization product exit from the top two stages; solid phase 204A of the devolatilization product stays in the devolatilization unit longer and then exits from the bottom stage. The gas phases 203A and 203B may be combined after they exit the devolatilization unit and before they enter the reformer reactor 301. The gas phases 203A and 203B and solid phase 204A can be introduced into the reformer reactor 301 as described in reference to FIG. 2A for a two-stage devolatilization unit.

Figure 4:
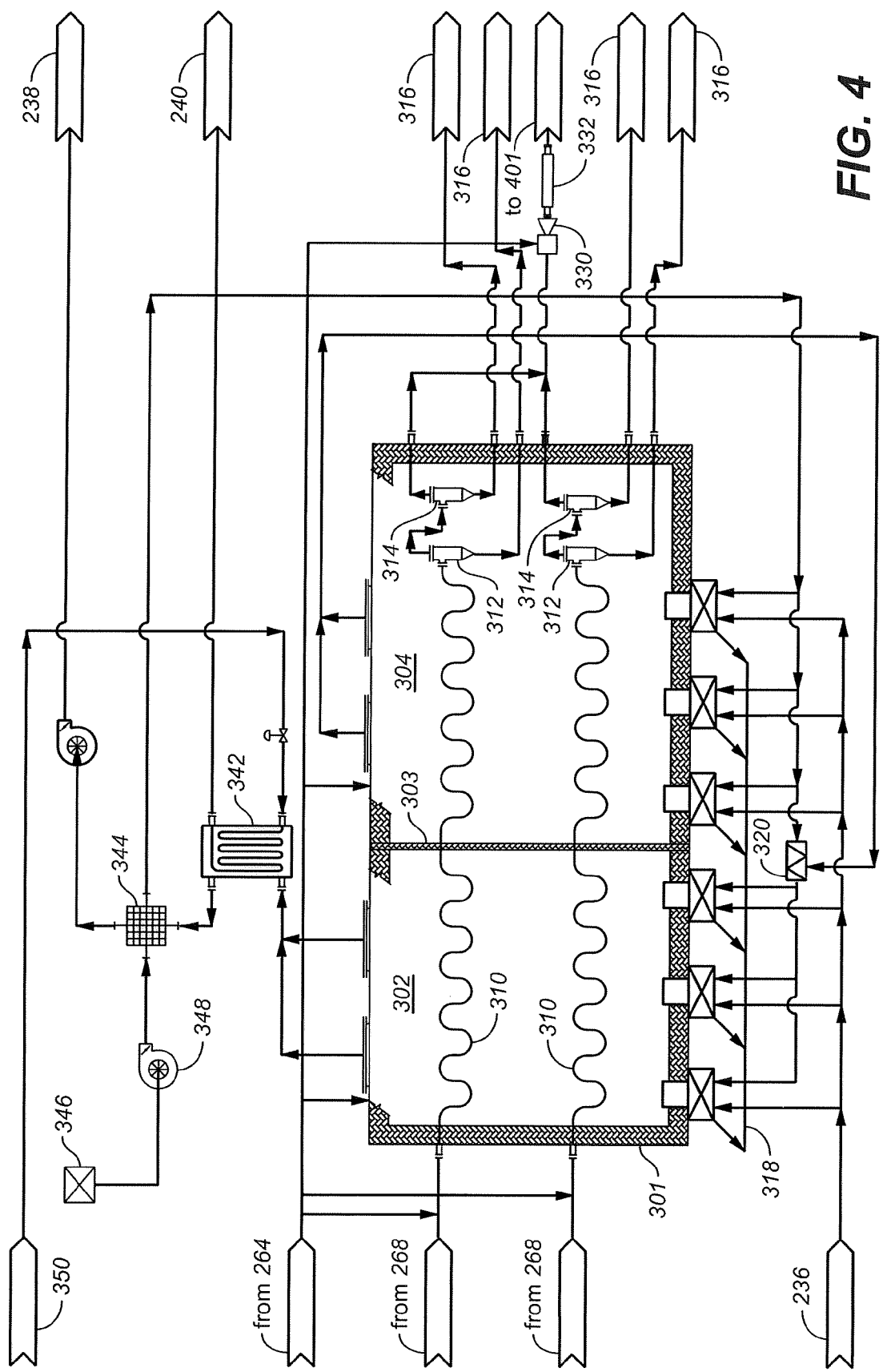
FIG. 4 shows a process flow for a reformer reactor, according to one variation.

FIG. 4 depicts an exemplary reformer reactor 301, which includes five major components: a cold chamber 302, a hot chamber 304, a set of burners 318, and a set of cyclones that includes a primary cyclone 312 and a polishing cyclone 314. A dividing wall 303 separates the cold chamber 302 from the hot chamber 304. Each chamber contains two separate serpentine or coiled reactor tubes 310, which increase the residence time of the products from the devolatilization unit 201 compared to the corresponding residence time for a linear tube. In some embodiments where the devolatilization product enters into the reformer reactor 301 directly, each serpentine or coiled reactor tube 310 is fed by each devolatilization stack 701. One devolatilization stack 701 can feed one reformer reactor 301. In other embodiments, each serpentine or coiled reactor tube 310 is fed by one-half of the reaction product from the burner 268, shown in FIG. 2A.

Each reactor tube 310 is connected to a primary cyclone 312, which is further connected to a polishing cyclone 314. Both cyclones remove ash from the product that exits from the reactor tubes 310. In certain embodiments, about 90% and 10% by weight solids, respectively, are removed by the primary cyclones 312 and polishing cyclones 314. The ash is directed to ash collectors 316. As illustrated in FIG. 1, and described in detail herein above, oxygen or a mixture of oxygen and steam may be optionally added at any point in the system, such as before, during, or after the devolatilization product passes through the reformer reactor 301.

In some embodiments, the reactor tubes 310 in the cold chamber 302 raise the temperature of the devolatilization products from about 700-1100° F. at the entrance of the reformer reactor 301 to a temperature of about 1200-1500° F. at the end of the cold chamber 302. In preferred embodiments, the temperature is kept below the softening point of the ash components to facilitate their later removal. The serpentine or coiled reactor tubes 310 in the hot chamber 304 and their contents are maintained at a constant temperature, such as about 1400° F. or some other suitable temperature.

In some embodiments, the temperatures of the cold chamber 302 and the hot chamber 304 stay above the dew point of the product from the devolatilization unit 201. The temperature of the hot chamber 304 can be about 1500° F., 1600° F., 1700° F., or higher. Using appropriate materials, the temperature for the reformer reactor 301 can be about 2000° F. or even higher. In various embodiments, the pressure of the reformer reactor 301 is between about 25-500 psig, such as about 50-200 psig. The pressure of the reformer reactor 301 can be the same as that for the devolatilization unit 201, in some embodiments.

In some embodiments, the reforming and/or partial-oxidation catalyst(s) that are (i) present in the product from the devolatilization unit 201 or are (ii) added to the reformer reactor 301, are entrained catalysts. In some embodiments, a fixed-bed or fluidized-bed reformer reactor 301 with one or more reforming and/or partial-oxidation catalyst(s) is used.

The reformer reactor 301 can be heated by a set of burners 318, which are fed by fuel gas 236 and a gas mixture exiting from a reformer air mixer 320. Fuel supplied to the burners 318 to provide heat for reactions to form syngas can be from any or all of three process sources: (1) "fresh" syngas from upstream sources; (2) unreacted product gas from downstream synthesis; and/or (3) natural gas.

The syngas exiting from the polishing cyclones 314 may be introduced to a quench and compressing section 401 of FIG. 1 directly. Alternatively or additionally, syngas can first enter into an eductor 330, where the syngas is joined with the oxygen/steam mixture from the reformer feed steam/oxygen mixer 264 (shown in FIG. 2A). The mixture is then optionally introduced to a feed/oxygen reactor 332 and ultimately into the quench and compressing section 401. If desired, the oxygen/steam mixture can also be introduced directly to both or either chambers of the reformer reactor 301. A standard flow valve (not shown), or some other known means, can be used to control the amount of the oxygen added to the system.

In some embodiments, reforming and partial oxidation occur in the same reaction vessel. In other embodiments, reforming and partial oxidation occur in different reaction vessels. For example, a partial-oxidation reactor (such as a fluidized, packed-bed, or microchannel reactor) can be upstream or downstream of the reformer reactor 301. In one embodiment, a partial-oxidation reactor is upstream of the reformer reactor 301 and generates heat for reforming in the reformer reactor 301.

After exiting the reformer reactor 301, syngas is preferably quickly cooled with water (or by some other means) to avoid formation of carbon. For example, the syngas product can be cooled with boiler feed water in the quench and compressing section 401. In one illustrative embodiment, boiler feed water of a temperature of about 200° F. is injected directly into the syngas stream to cool the temperature of the stream from about 1400° F. to about 1000° F.

Syngas pressure is preferably increased prior to conditioning. In some embodiments, the syngas is compressed to about 1000 psig, 1500 psig, 2000 psig, or higher. In some embodiments, syngas conditioning 501 comprises feeding the syngas to a $CO_2$ removal system (shown in FIG. 1). Any methods known in the art can be employed to remove carbon dioxide, including membrane-based or solvent-based separation methods. In some embodiments, little or no $CO_2$ is removed from the syngas.

In some embodiments, the syngas produced using the methods described herein has less impurities compared to syngas produced in the absence of any oxygen addition. In some embodiments, the decreased amount of impurities facilitates the further purification of syngas. For example, less energy or time may be required to remove $CO_2$ from the syngas produced using the methods described herein than from syngas produced in the absence of oxygen.

If desired, the removed $CO_2$ can be used anywhere an inert gas is desirable. For example, $CO_2$ can be used to convey or entrain solid material from one point to another point of the process. Another use of $CO_2$ is to vary the $H_2/CO$ ratio by the water-gas shift reaction. Recovered $CO_2$ can also be used to react with methane in dry reforming to produce syngas, or react with pure carbon (e.g., carbon deposited on reactor walls or catalyst surfaces) to form 2 moles of CO in the reverse Boudouard reaction (i.e., $CO_2 + C \leftrightarrow 2\ CO$).

In some embodiments, removed $CO_2$ can be recycled back to the devolatilization unit 201. Generally, a variety of purge streams from any operations downstream of the devolatilization can be recycled back to the devolatilization unit 201. These purge streams may contain CO, $CO_2$, $H_2$, $H_2O$, $CH_4$, and other hydrocarbons.

Cooled syngas can optionally be fed to a benzene, toluene, ethyl benzene, and xylenes removal system. In some embodiments, the removal system comprises a plurality of activated carbon beds. Of course, other organic compounds (such as tars) can be removed as well, depending on conditions.

Figure 5:
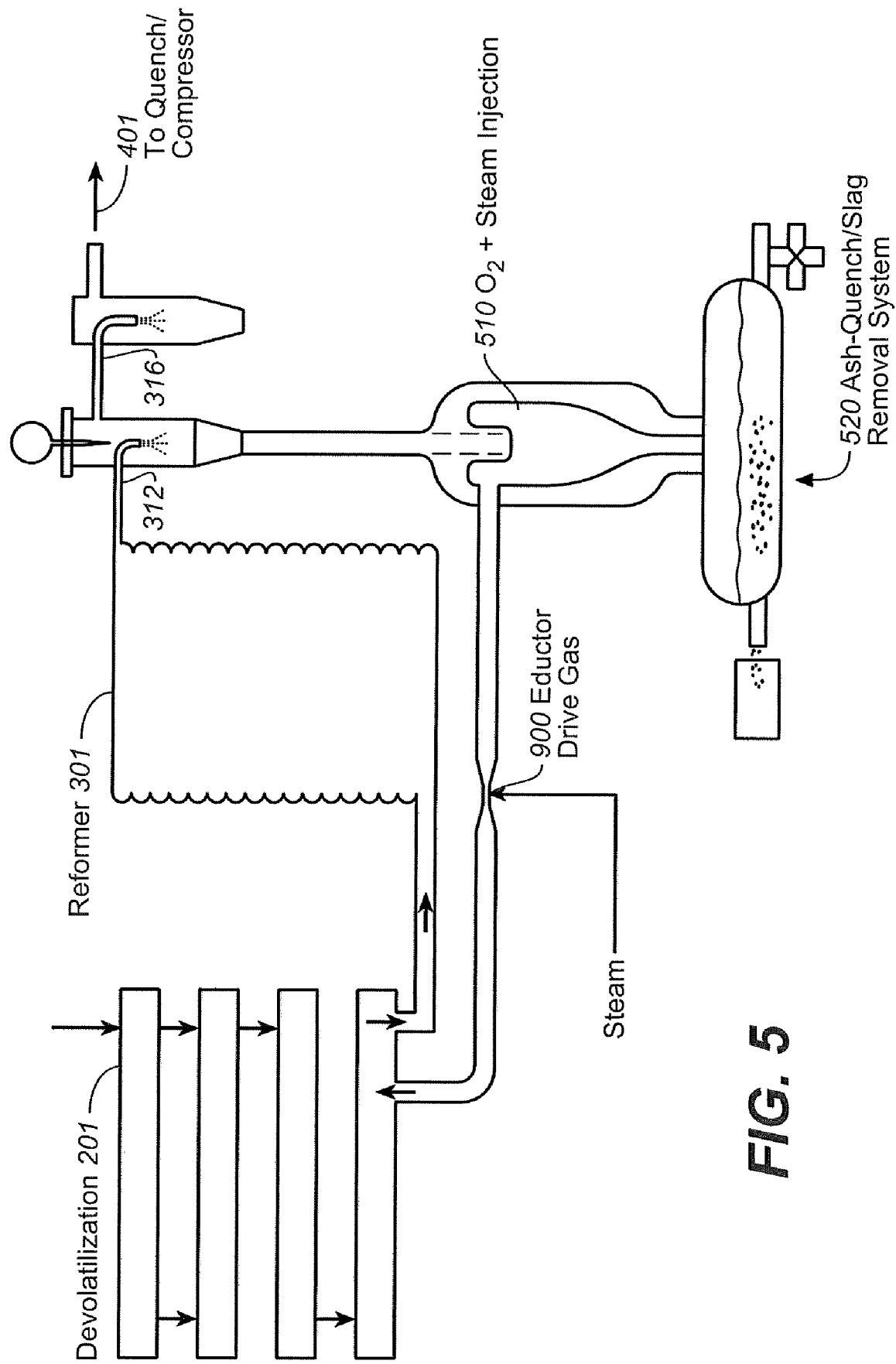
FIG. 5 shows a process flow for the injection of oxygen and steam into syngas that is recycled back to the devolatilization unit, according to one variation.

FIG. 5 depicts certain embodiments for devolatilization and reforming. The feed material is introduced into a devolatilization unit 201. The product that exits from the devolatilization unit 201 is introduced into a reformer reactor 301, where syngas is produced. The syngas produced in the reformer reactor 301 is introduced into a primary cyclone 312 and a polishing cyclone 314, where ash and other solids are removed from the syngas product. The syngas that exits from the polishing cyclone 314 is introduced to a quench and compressing section 401, where the syngas is cooled and compressed. The solids separated from the syngas product in the primary cyclone 312 are introduced into an ash-quench/slag-removal system 520, where oxygen or a mixture of oxygen and steam can be injected. The mixture of oxygen and steam allows the solids separated from the syngas to undergo partial oxidation. The gas product from the ash-quench/slag-removal system 520 is introduced to an eductor 900, which helps the gas product transfer back to the devolatilization unit 201. The gas product circulating back from the ash-quench/slag removal system 520 helps to move forward the material in the devolatilization unit 201. In one embodiment, the gas product from the ash-quench/slag removal system 520 enters the devolatilization unit 201 near the exit of the devolatilization unit. The solids further separated in the ash-quench/slag-removal system 520 are removed at the bottom of the system.

Another aspect of the present invention relates to eductors. Eductors (also known as jet ejector pumps or Venturi pumps) are an efficient way to pump or move many types of liquids and gases. Eductors generally utilize the kinetic energy of one species to cause the flow of another. In operation, the pressure energy of the motive liquid is converted to velocity energy by a converging nozzle. The high velocity flow then entrains another species (such as solids from the devolatilization unit 201). The mixture is then converted back to an intermediate pressure after passing through a diffuser. Eductors can also balance pressure drops and aid in overall heat transfer.

In some embodiments, the eductor is used to convey the material leaving the devolatilization unit 201 and entering the reformer reactor 301 (such as eductor 266 shown in FIG. 2A). In certain embodiments, the drive gas for this eductor is steam and/or oxygen that is introduced into the reformer reactor 301.

Figure 6:
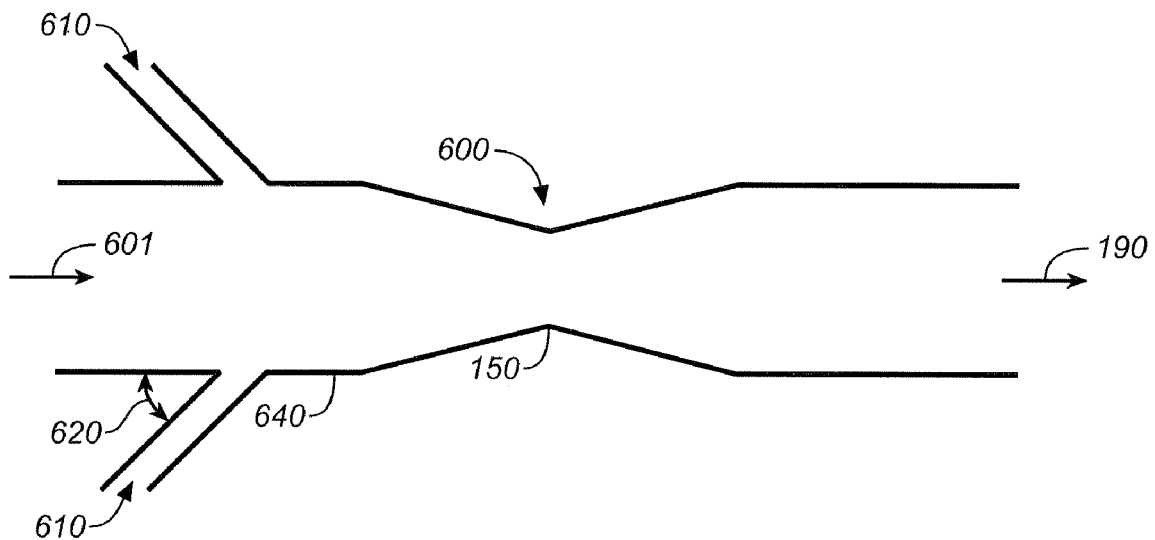
FIG. 6 shows an eductor, according to one variation.

An eductor 600 that can be used in particular embodiments is depicted in FIG. 6, which is exemplary and non-limiting. With reference to FIG. 6, generally solids and (if present) gases enter as stream 601, which can be referred to as the motive phase. In some embodiments, additional vapor is added in streams 610, which collectively can be referred to interchangeably as the suction fluid, the educted fluid, or the eductor drive fluid.

The eductor 600 in FIG. 6 is characterized by a first cross-sectional area 640 and a second, smaller cross-sectional area 150. The area reduction causes a lower pressure, which creates a suction effect to pull material forward. The material velocity increases through the smaller area 150, and then returns to a lower velocity downstream of the area reduction, according to a momentum balance. Stream 190 exits the eductor 600.

Streams 610 are shown in FIG. 6 to enter at an angle denoted 620. This angle can be any angle but in some embodiments is greater than about 0 degrees and less than about 90 degrees. An angle of 0 degrees produces co-incident flow of the suction fluid and the motive phase, while an angle of 90 degrees produces perpendicular injection of the suction fluid into the eductor. An angle of greater than 90 degrees, and up to 180 degrees, represents injection of the suction fluid in a direction flowing upstream relative to the movement of the motive phase. Exemplary angles of entry in various embodiments include angles between about 10 to about 60 degrees, and in certain embodiments, the angle is about any of 30, 35, 40, or 45 degrees.

While FIG. 6 shows two streams 610 entering the eductor 600, other embodiments can include 1, 3, 4, 5, or more locations where suction-fluid enters the eductor 600. By "streams 610" it is meant any number of actual streams, including a single stream of suction fluid. These different entries can all be characterized by the same angle. Alternatively, different angles may be used.

According to embodiments of the present invention, stream 601 can be at least a portion of the solid-vapor mixture exiting the devolatilization unit 201. Stream 601 can enter the eductor 600 by means of a single-screw (auger) conveyer, a twin-screw device, or by any other means. Streams 610 can be one or more of steam, oxygen, and air. The amount of steam or oxygen to inject by means of streams 610 can be the amount that is desired for the steam reforming and/or partial-oxidation steps downstream of the devolatilization unit 201, or can be a different amount.

In addition to adding reactants to the process, streams 610 also can enhance mixing efficiency within the eductor 600, so that species can be well-mixed upon entering the reformer reactor 301. Without being limited to any particular theory, it is believed that the solid material entering in stream 601 is characterized by laminar flow or plug flow; the suction fluid from 610 is thought to cause an onset of turbulent flow within the eductor 600. Turbulence is known to enhance mixing and can also help break apart the solids and reduce particle size. The exact nature of this onset of turbulence is generally a function of the velocity and pressure of streams 601 and 610, the areas 640 and 150, the angle 620 (or plurality of angles), and the nature of the motive and suction fluids. The eductor 600 can also be suitable for multiphase annular flow from the devolatilization unit 201 to said heated reaction vessel 301.

As will be appreciated, other gases besides $H_2O$ and $O_2$ for streams 610 can additionally or alternatively be used. Other gases that could be used include, but are not limited to, recycled syngas, recycled steam possibly containing various impurities, such as $CO_2$, $N_2$, methanol vapor, ethanol vapor, etc.

The eductor 600 can be employed in any step of the process described herein, such as the removal of ash-rich solids or other purge streams (such as eductor 330 in FIG. 4) or the mixing of oxygen and steam with syngas (such as eductor 900 in FIG. 5). Eductor 600 can also be used in any other apparatus for which an eductor is desirable, such as an apparatus for which one or more decreases in pressure within the apparatus is desirable.

Figure 7:
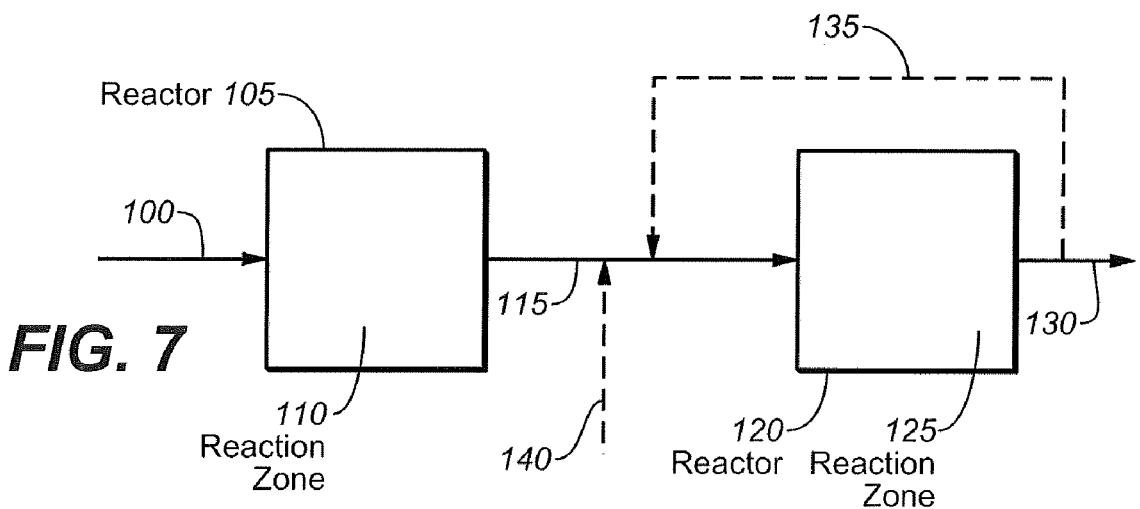
FIG. 7 shows a process flow for producing methanol and ethanol from syngas using two reactors in sequence, according to one variation.

Exemplary methods and apparatus for producing alcohols from syngas are disclosed herein. In some variations of these methods and apparatus, syngas is catalytically converted to methanol in a first reaction zone, and residual syngas from the first reaction zone is then catalytically converted to ethanol in a second reaction zone. Referring to FIG. 7, for example, in one variation a syngas feedstream 100 is introduced into a first reactor 105 comprising a first reaction zone 110. One or more catalysts in reaction zone 110 convert at least a portion of syngas feedstream 100 to methanol to provide an intermediate product stream 115 comprising at least a portion of the residual (unreacted) syngas from feedstream 100, methanol, and, in some variations, higher alcohols and/or other reaction products.

At least a portion of intermediate product stream 115 is introduced into a second reactor 120 comprising a second reaction zone 125. One or more catalysts in reaction zone 125 convert at least a portion of syngas from intermediate product stream 115 and/or at least a portion of methanol from intermediate product stream 115 to provide a product stream 130 comprising ethanol and, in some variations, methanol, higher alcohols, other reaction products, and/or unreacted syngas from intermediate product stream 115.

Various components of product stream 130 such as, for example, methanol, ethanol, alcohol mixtures (e.g., methanol, ethanol, and/or higher alcohols), water, and unreacted syngas may be separated out and (optionally) purified by the methods described herein or conventional methods. Such methods may include, for example, condensation, distillation, and membrane separation processes, as well as drying or purifying with molecular sieves.

Syngas feedstream 100 may be produced in any suitable manner known to one of ordinary skill in the art from any suitable feedstock. In some variations, syngas feedstream 100 is filtered, purified, or otherwise conditioned prior to being introduced into reactor 105. For example, carbon dioxide, benzene, toluene, ethyl benzene, xylenes, sulfur compounds, metals, and/or other impurities or potential catalyst poisons may be removed from syngas feedstream 100 by conventional methods known to one of ordinary skill in the art.

In some variations, syngas feedstream 100 comprises $H_2$ and CO at an $H_2$/CO ratio having a value between about 0.5 to about 3.0, about 1.0 to about 1.5, or about 1.5 to about 2.0. The $H_2$/CO ratio in feedstream 100 can, in some variations, affect the yield of methanol and other products in reactor 105. The preferred $H_2$/CO ratio in such variations may depend on the catalyst or catalysts used in reactor 105 as well as on the operating conditions. Consequently, in some variations, the production and/or subsequent conditioning of syngas feedstream 100 is controlled to produce syngas having a $H_2$/CO ratio within a range desired to optimize, for example, production of methanol, ethanol, or both methanol and ethanol.

Syngas feedstream 100 may optionally be pressurized and/or heated by compressors and heaters (not shown) prior to entering reactor 105. In some variations, syngas feedstream 100 enters reactor 105 at a temperature of about 300° F. to about 600° F. and at a pressure of about 500 psig to about 2500 psig.

Reactor 105 may be any type of catalytic reactor suitable for the conversion of syngas to methanol, alcohol mixtures comprising methanol, higher alcohols, and/or other products. Reactor 105 may be any suitable fixed-bed reactor, for example. In some variations, reactor 105 comprises tubes filled with one or more catalysts. Syngas passing through the tubes undergoes catalyzed reactions to form methanol and, in some variations, higher alcohols or other products. In some embodiments, catalysis occurs within pellets or in a homogeneous phase. Reactor 105 may operate, for example, at temperatures of about 400° F. to about 700° F. and at pressures of about 500 psig to about 2500 psig.

Any suitable catalyst or combination of catalysts may be used in reactor 105 to catalyze reactions converting syngas to methanol and, optionally, to higher alcohols and/or other products. Suitable catalysts may include, but are not limited to, one or more of $ZnO/Cr_2O_3$, $Cu/ZnO$, $Cu/ZnO/Al_2O_3$, $Cu/ZnO/Cr_2O_3$, $Cu/ThO_2$, Co/Mo/S, Co/S, Mo/S, Ni/S, Ni/Mo/S, Ni/Co/Mo/S, Rh, Ti, Fe, Ir, and any of the foregoing in combination with Mn and/or V. The addition of basic promoters (e.g. K, Li, Na, K, Rb, Cs, and Fr) increases the activity and selectivity of some of these catalysts for alcohols. Basic promoters include alkaline-earth and rare-earth metals. Non-metallic bases can also serve as effective promoters in some embodiments.

In some variations, up to about 50% of CO in syngas feedstream 100 is converted to methanol in reaction zone 110. Intermediate product stream 115 output from reactor 105 may comprise, in some variations, about 5% to about 50% methanol, about 5% to about 50% ethanol, about 5% to about 25% CO, about 5% to about 25% $H_2$, and about 2% to about 35% $CO_2$, as well as other gases. In some embodiments, intermediate product stream 115 also comprises one or more higher alcohols, such as ethanol, propanol, or butanol.

The $H_2$/CO ratio in intermediate product stream 115 can, in some variations, affect the yield of ethanol and other products in reactor 120. The preferred $H_2$/CO ratio in such variations may depend on the catalyst or catalysts used in reactor 120 as well as on the operating conditions. The $H_2$/CO ratio in intermediate product stream 115 can differ from that of feedstream 100 as a result of reactions occurring in reactor 105. In some variations, the $H_2$/CO ratio of intermediate product stream 115 provides a higher ethanol yield in reactor 120 than would the $H_2$/CO ratio of feedstream 100. In such variations, operation of reactor 105 to produce methanol, for example, improves the $H_2$/CO ratio of the syngas fed to reactor 120 from the standpoint of ethanol yield in reactor 120.

In one example, feedstream 100 comprises syngas with an $H_2$/CO ratio of about 1.5 to about 2, and the preferred $H_2$/CO ratio for production of ethanol in reactor 120 is about 1. Operation of reactor 105 to produce methanol, in this example, depletes $H_2$ in the syngas which decreases the $H_2$/CO ratio in intermediate product stream 115 to a value closer to 1 and thus improves the ethanol yield in reactor 120. In certain embodiments, the catalyst is a Cu/ZnO/alumina catalyst.

Reactor 120 may be any type of catalytic reactor suitable for the conversion of syngas, methanol, and/or syngas plus methanol to ethanol and, optionally, to higher alcohols and/or other products. Reactor 120 may be any suitable fixed-bed reactor, for example. In some variations, reactor 120 comprises tubes filled with one or more catalysts. Syngas and/or methanol passing through the tubes undergoes surface catalyzed reactions to form ethanol and, in some variations, higher alcohols and/or other products. While not intending to be bound by any particular theory, it is presently believed that the methanol may be converted to syngas and thence to ethanol, the methanol may be converted directly to ethanol via a homologation reaction, and/or the methanol may be converted to ethanol by other mechanisms. Reactor 120 may operate, for example, at temperatures of about 500° F. to about 800° F. and at pressures of about 500 psig to about 2500 psig.

Any suitable catalyst or combination of catalysts may be used in reactor 120 to catalyze reactions converting syngas, methanol, and/or syngas+methanol to ethanol and, optionally, to higher alcohols and/or other products. Suitable catalysts may include, but are not limited to, alkali/$ZnO/Cr_2O_3$, $Cu/ZnO$, $Cu/ZnO/Al_2O_3$, $CuO/CoO$, $CuO/CoO/Al_2O_3$, Co/S, Mo/S, Co/Mo/S, Ni/S, Ni/Mo/S, Ni/Co/Mo/S, Rh/Ti/$SiO_2$, Rh/Mn/$SiO_2$, Rh/Ti/Fe/Ir/$SiO_2$, Rh/Mn/MCM-41, Cu, Zn, Rh, Ti, Fe, Ir, and mixtures thereof. The addition of basic promoters (e.g. K, Li, Na, Rb, Cs, and Fr) may increase the activity and selectivity of some of these catalysts for ethanol or other $C_{2+}$ alcohols. Basic promoters include alkaline-earth and rare-earth metals. Non-metallic bases can also serve as effective promoters, in some embodiments.

In some embodiments, catalysts for reactor 120 include one or more of $ZnO/Cr_2O_3$, $Cu/ZnO$, $Cu/ZnO/Al_2O_3$, $CuO/CoO$, $CuO/CoO/Al_2O_3$, Co/S, Mo/S, Co/Mo/S, Ni/S, Ni/Mo/S, Ni/Co/Mo/S, Rh/Ti/$SiO_2$, Rh/Mn/$SiO_2$, Rh/Ti/Fe/Ir/$SiO_2$, Rh/Mn/MCM-41, Ni/Mo/S, Ni/Co/Mo/S, and any of the foregoing in combination with Mn and/or V. Again, any of these catalysts can (but do not necessarily) include one or more basic promoters.

Product stream 130 output from reactor 120 may comprise, in some variations, about 0% to about 50% methanol, about 10% to about 90% ethanol, about 0% to about 25% CO, about 0% to about 25% $H_2$, and about 5% to about 25% $CO_2$, as well as other gases. In some embodiments, product stream 130 also comprises one or more higher alcohols, such as propanol or butanol.

Referring again to FIG. 7, in some variations unreacted syngas in product stream 130 is separated from product stream 130 to form feedstream 135 and recycled through reactor 120 to further increase, for example, the yield of ethanol and/or other desired products. Alternatively, or in addition, in some variations unreacted syngas in product stream 130 is recycled through reactor 105 by adding it to syngas feedstream 100. The latter approach may be unsuitable, however, if the unreacted syngas in product stream 130 is contaminated, for example, with sulfur, sulfur compounds, metals, or other materials that can poison methanol catalysts in reactor 105.

Also, in some variations a methanol feedstream 140 is added to intermediate product stream 115 or otherwise introduced to reactor 120 to further increase, for example, the yield of ethanol and/or other desired products. For example, methanol in product stream 130 may be separated (not shown) from product stream 130 to form feedstream 140 and then recycled through reactor 120. Methanol from other sources may be introduced into reactor 120, as well or instead.

In some variations, one or more catalysts in reactor 105, one or more catalysts in reactor 120, or one or more catalysts in both reactor 105 and reactor 120 catalyze the conversion of $CO_2$ to methanol. Production of methanol in reactor 105, reactor 120, or in both reactors may be thereby enhanced by consumption of $CO_2$ present in syngas feedstream 100. Consequently, in some variations, $CO_2$ is added to syngas feedstream 100, or the production and/or subsequent conditioning of syngas feedstream 100 is controlled to produce syngas having a desirable amount of $CO_2$. Suitable catalysts for converting $CO_2$ to methanol may include, in some variations, one or more of those listed above for use in reactors 105 and 120. Enhanced production of methanol by consumption of $CO_2$ may result, in some variations, in enhanced production of ethanol by conversion of the methanol to ethanol and/or by a resulting favorable adjustment of the $H_2/CO$ ratio in the syngas stream introduced to reactor 120.

Figure 8:
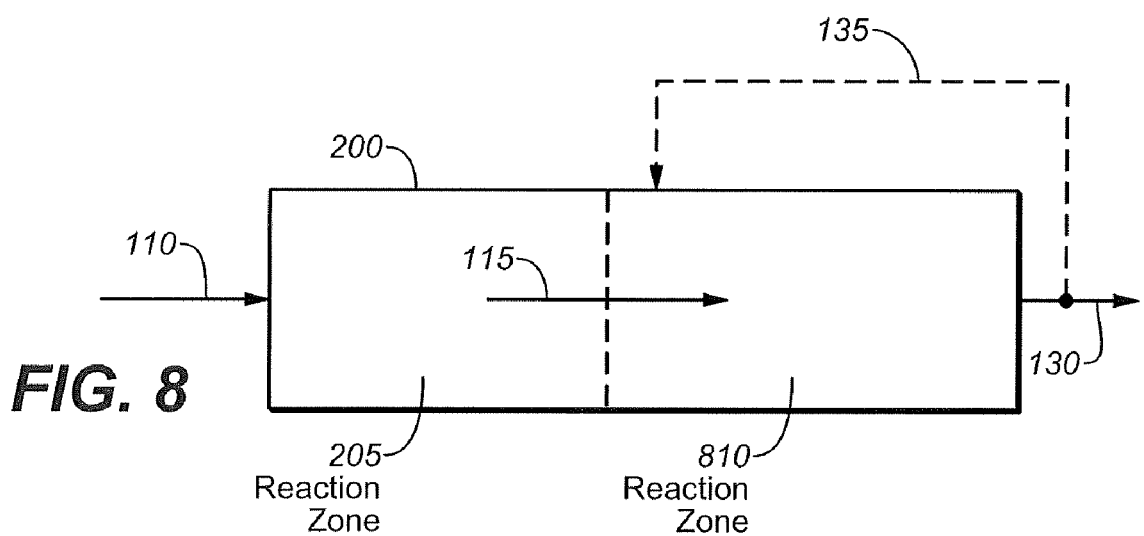
FIG. 8 shows a process flow for producing methanol and ethanol from syngas using two reaction zones in sequence in a single reactor, according to one variation.

Referring now to FIG. 8, some alternative variations differ from those described above primarily by use of a single reactor 200 comprising a first reaction zone 205 and a second reaction zone 810 rather than two reactors. Syngas feedstream 100 is introduced into first reaction zone 205, where one or more catalysts convert at least a portion of syngas feedstream 100 to methanol to provide intermediate product stream 115 (comprising at least a portion of the unreacted syngas from feedstream 100, methanol and, in some variations, higher alcohols and/or other reaction products). At least a portion of intermediate product stream 115 is introduced into second reaction zone 810, where one or more catalysts convert at least a portion of syngas from intermediate product stream 115 and/or at least a portion of methanol from intermediate product stream 115 to form product stream 130 comprising ethanol and, in some variations, methanol, higher alcohols, other reaction products, and/or unreacted syngas from intermediate product stream 115.

Reactor 200 may be any type of suitable catalytic reactor comprising two or more reaction zones. Operation of reactor 200 may be similar to the operation of reactors 105 and 120 described above. In particular, in some variations, the catalysts used in reactions zones 205 and 810 and the operating conditions for the reaction zones are the same as or similar to those for, respectively, reaction zones 110 and 120 described above. The compositions of intermediate product stream 115 and product stream 130 may, in some variations, be the same as or similar to those for the variations described above with respect to FIG. 7. Syngas in product stream 130 may be recycled through reaction zone 810 or added to feedstream 100. $CO_2$ may be added to syngas feedstream 100, or the production and/or subsequent conditioning of syngas feedstream 100 may be controlled to produce syngas having a desirable amount of $CO_2$ for enhanced methanol production. A methanol feedstream (not shown) may be introduced to reaction zone 810 to further increase, for example, the yield of ethanol and/or other desired products. This methanol feedstream may be, for example, separated from product stream 130.

Similarly to the two-reactor variations, in some of the single-reactor variations the $H_2/CO$ ratio in intermediate product stream 115 can affect the yield of ethanol and other products in reaction zone 810. In some variations, the $H_2/CO$ ratio of intermediate product stream 115 differs from that of feedstream 100 and provides a higher ethanol yield in reaction zone 810 than would the $H_2/CO$ ratio of feedstream 100. In such variations, production of methanol in reaction zone 205, for example, improves the $H_2/CO$ ratio of the syngas fed to reaction zone 810 from the standpoint of ethanol yield in reactor 120.

Figure 9:
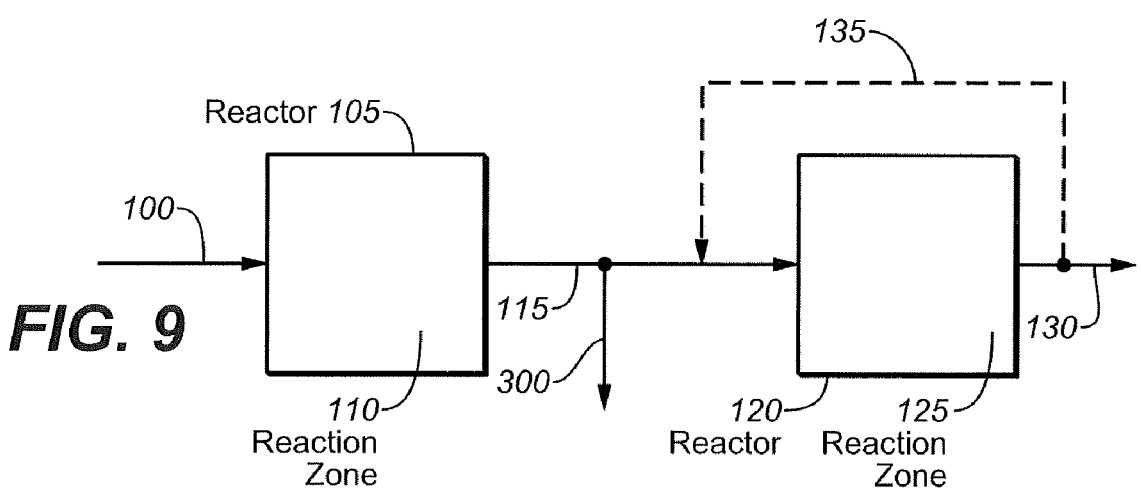
FIG. 9 shows a process flow for producing methanol and ethanol from syngas using two reactors in sequence, with at least some of the methanol produced in the first reactor diverted from the second reactor, according to one variation.

Referring now to FIG. 9, some alternative variations differ from those described with respect to FIG. 7 in that at least a portion (some or substantially all) of the methanol in intermediate product stream 115 is diverted into a methanol product stream 300 prior to the introduction of product stream 115 into reactor 120. Methanol in product stream 300 can be separated and purified by conventional methods, for example. As above, in some of these variations the $H_2/CO$ ratio of intermediate product stream 115 differs from that of feedstream 100 and provides a higher ethanol yield in reactor 120 than would the $H_2/CO$ ratio of feedstream 100. Hence, the production of methanol in reactor 105 may advantageously enhance ethanol production in reactor 120 in some of these variations.

Figure 11:
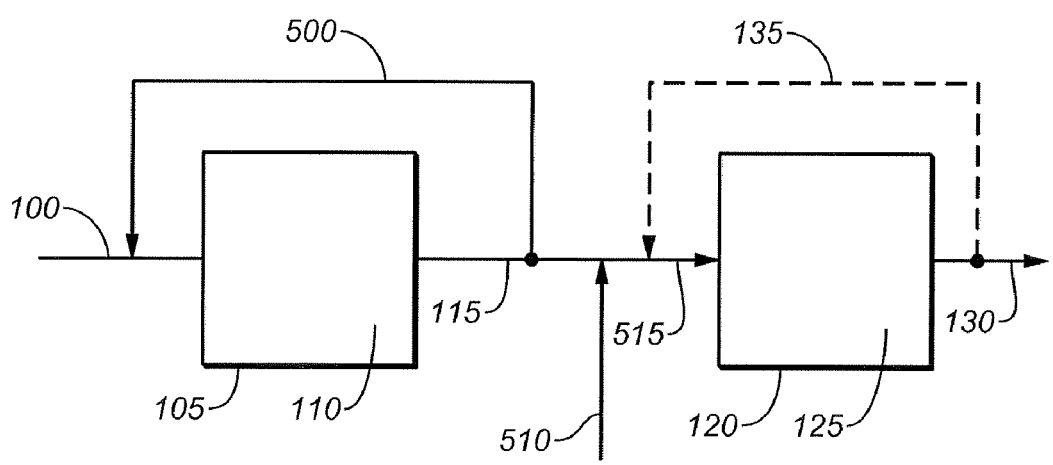
FIG. 11 shows a process flow for producing methanol and ethanol from syngas using two reactors in sequence, with the first reactor producing methanol in high yield for conversion to ethanol in the second reactor, according to one variation.

In some variations methanol is produced at high yield in a first reactor and subsequently converted to ethanol in a second reactor. Referring to FIG. 11, for example, in some variations a syngas feedstream 100 is catalytically converted to methanol in a first reactor 105 at a yield (mole conversion of CO to methanol) of, for example, at least 50%, 75%, 85%, 95%, or higher, subject to equilibrium constraints. High methanol yields may be facilitated, for example, by separating out some or substantially all of the non-methanol components in intermediate product stream 115 as a stream 500 that is recycled through reactor 105.

An unrecycled portion of intermediate product stream 115, rich in methanol, is (optionally) mixed with another syngas feedstream 510 to provide feedstream 515 which is introduced into reactor 120. At least a portion of the methanol and (optionally) syngas introduced into reactor 120 are catalytically converted to provide a product stream 130 comprising ethanol and, in some variations, methanol, higher alcohol, other reaction products, and/or unreacted syngas from feedstream 515. In some variations, unreacted syngas in product stream 130 is recycled through reactor 120 as feedstream 135 and/or recycled through reactor 105. Various components of product stream 130 may be separated out and/or purified as described above, for example.

In some variations, the ratio of methanol to CO in a feedstream may be adjusted, for example, to optimize the yield of ethanol in reactor 120. In some embodiments, the ratio of methanol/CO in reactor 120 is between about 0.5 to about 2.0. In particular embodiments, the ratio of methanol/CO in reactor 120 is about 1.0.

Any suitable catalyst or combination of catalysts may be used in reactor 105. Suitable catalysts for reactor 105 may include, but are not limited to, the methanol catalysts listed above. Similarly, any suitable catalyst or combination of catalysts may be used in reactor 120. Suitable catalysts for reactor 120 may include, but are not limited to, the ethanol catalysts listed above.

The composition of catalysts in reactors 105 and 120, or reaction zones 110 and 125, can be similar or even the same.

Reference to a "first catalyst" and "second catalyst" in conjunction with reaction zones is a reference to different physical materials, not necessarily a reference to different catalyst compositions.

In variations of any of the methods described herein that use a first reaction zone and a second reaction zone, the initial syngas stream is introduced into both the first reaction zone and the second reaction zone, such as the independent introduction of syngas into both the first reaction zone and the second reaction zone. In some embodiments, the syngas is from an external source. In some embodiments, the syngas is from any of the methods described herein (such as residual syngas from a first reaction zone or a second reaction zone).

In some embodiments of any of the methods described herein, syngas from any source is added to the first reaction zone and/or the second reaction zone. In some embodiments of any of the methods described herein, methanol from any source is added to the second reaction zone.

Certain embodiments employ a plurality of physical reactors in one or both of the reaction zones. For example, the first zone could consist of two reactors, followed by a single reactor as the second zone. Or, in another example, the first zone could be one reactor followed by two reactors in the second zone. In general, any "zone" or "reaction zone" can contain a fraction of one, two, three, or more physical reactors.

In some embodiments of any of the methods described herein, reaction conditions (such as temperature and pressure) used for the conversion of syngas to methanol, the conversion of syngas and/or methanol to ethanol, or the homologation of methanol to ethanol, are the same as those described in any of U.S. Pat. Nos. 4,371,724; 4,424,384; 4,374,285; 4,409,405; 4,277,634; 4,253,987; 4,233,466; and 4,171,461; all of which are incorporated by reference herein in their entirety. If desired, one skilled in the art can adjust reaction conditions using standard methods to improve the production of methanol and/or ethanol.

Figure 10:
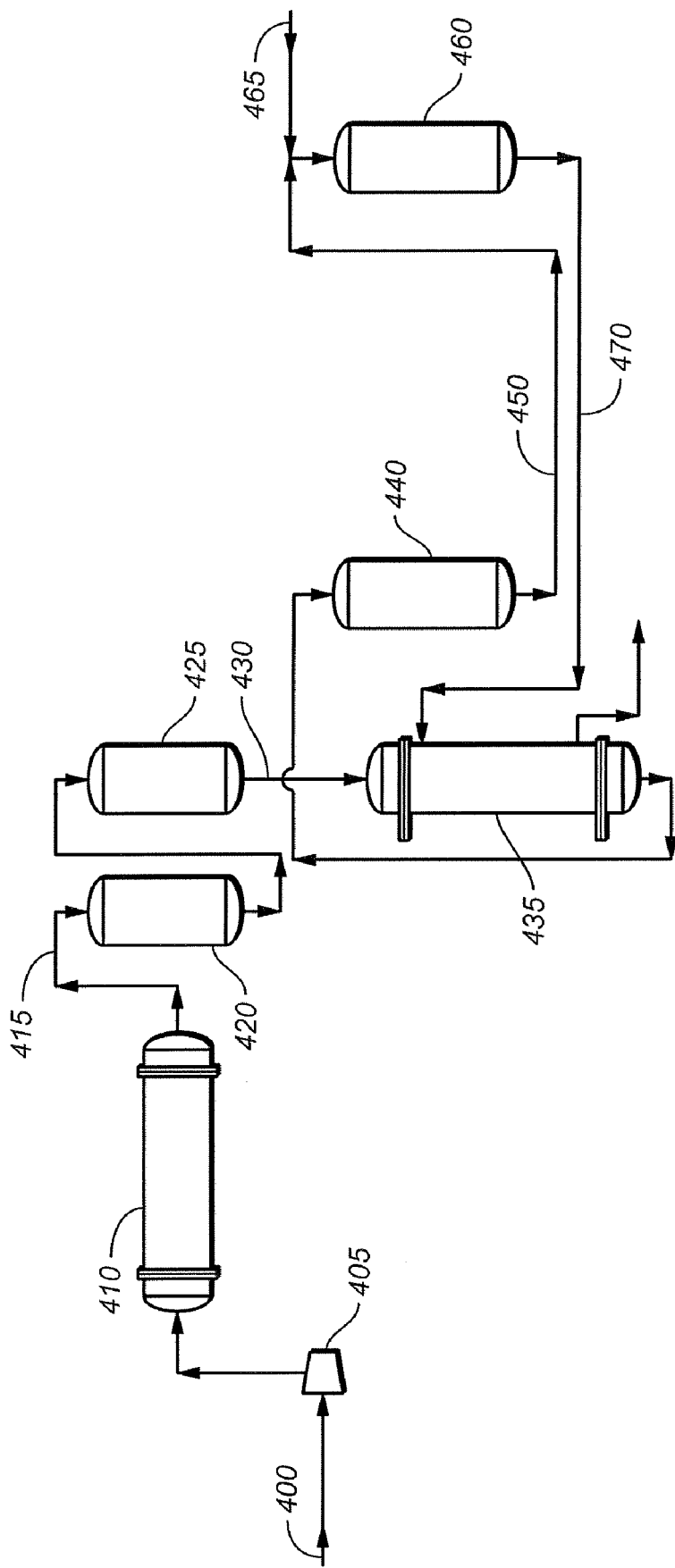
FIG. 10 shows a process flow for producing methanol and ethanol from syngas using two reactors in sequence according to another variation.

FIG. 10 shows another example, in more detail than above, of a process in which syngas is catalytically converted to methanol in a first reactor, and methanol and residual syngas from the first reactor are converted to ethanol in a second reactor. Referring now to FIG. 10, a single two-stage intercooled reciprocating compressor 405 compresses syngas feedstream 400 to about 1500 psig and feeds it at a temperature of about 135° F. to syngas preheater 410. Preheater 410 is a shell and tube heat exchanger that uses steam as an enthalpy source.

Heated syngas 415 from preheater 410 is sent to a set of reactor guard beds 420, 425. Guard beds 420, 425 can be configured in a permanent lead-lag arrangement but are piped such that either bed can be bypassed. The piping arrangement allows one bed to be in service while the other is being regenerated or activated. Regeneration/activation is initiated by a mixed hydrogen and nitrogen line (not shown). Guard beds 415, 420 remove, for example, sulfurs and metals that may poison the methanol catalysts. In some embodiments, one or more catalyst poisons are removed by adsorption over copper, copper chromite, nickel, cobalt, or molybdenum. These and other metals can be supported on high-surface-area refractory inorganic oxide materials such as alumina, silica, silica/alumina, clays, or kieselguhr. One exemplary material is copper on alumina.

Exit gases 430 from guard beds 420, 425 are sent to an alcohol reactor cross exchanger 435 at about 350° F. and are heated to about 480° F. during heat exchange with crude alcohol exit gases 470 from second alcohol reactor 460.

Syngas at about 1500 psig and about 480° F. enters a first alcohol synthesis reactor 440, where at least a portion of the syngas undergoes a surface-catalyzed reaction in supported catalyst tubular reactors within the reactor vessel. In some variations, the catalyst in reactor 440 is a Cu/ZnO/alumina catalyst. Methanol is expected to be formed via the reaction $CO+2H_2 \rightarrow CH_3OH$. In some variations methanol may be formed, as well, by hydrogenation of $CO_2$.

Product gases 450 leave alcohol synthesis reactor 440 at a temperature of about 500° F. and enter alcohol synthesis reactor 460. In addition, a methanol stream 465 (e.g., a methanol recycle stream separated from crude alcohol stream 470) is mixed with the product gases 450 from reactor 440 and also introduced to reactor 460. Reactions occurring in reactor 460 include ethanol formation at about a 40% molar conversion basis of methanol entering reactor 460.

Crude alcohol stream 470 exits reactor 460 at a temperature of about 650° F. and is cooled by heat exchange in alcohol reactor cross exchanger 435 to a temperature of about 530° F. Subsequent heat recovery and other cooling steps (not shown) cool crude alcohol stream 470 to about 100° F.

Ethanol, methanol, residual syngas, and other components of crude alcohol stream 470 may be separated and (optionally) purified by using the methods described herein or using conventional methods (not shown). Syngas recovered from stream 470 may be recycled through the reactors by mixing it with syngas feedstream 400, for example.

In some embodiments, ethanol is purified from the product stream 130 or crude alcohol stream 470 by first drying the product stream 130 or crude alcohol stream 470 to produce an intermediate product, and then distilling the intermediate product to produce a purified ethanol product. In some embodiments, the product stream 130 or crude alcohol stream 470 comprises or consists of ethanol, methanol, propanol, butanol, and water. In some embodiments, product stream 130 or crude alcohol stream 470 includes one or more of the following alcohols: 1-propanol, 2-propanol, 1-butanol, 2-butanol, t-butanol, pentanols, hexanols, heptanols, and octanols, and/or higher alcohols. In some embodiments, product stream 130 or crude alcohol stream 470 includes one or more aldehydes, ketones, and/or organic acids (such as formaldehyde, acetaldehyde, acetic acid, and the like).

In particular embodiments, the drying step reduces the amount of water in the product stream 130 or crude alcohol stream 470 by at least about 75%, 95%, or more. In particular embodiments, the amount of the water is less than or equal to about 5% or preferably about 0.5% of the intermediate product by weight.

In some embodiments, the drying step involves passing the product stream 130 or crude alcohol stream 470 through a membrane, such as zeolite membrane, or through one or more molecular sieves to produce an intermediate product. Conventional distillation methods can be used to distill the intermediate product. In some embodiments, the distillation conditions are adjusted using standard methods based on the contents and/or purity of the distilled product being produced to increase the purity of ethanol in the final product. In some embodiments, ethanol is between about 95% to about 99.9% of the purified ethanol product by weight.

In some embodiments of the invention, one or more parameters are varied to improve or optimize the generation of syngas or downstream products (such as ethanol). For example, one or more parameters can be adjusted during the conversion of a feed material to syngas. In some embodiments, a feed material is converted to syngas using one set of conditions, and then the method is repeated for the same type of feed material, or another type of feed material, under a different set of conditions to improve the production of syngas. Standard statistical methods can be used to help determine which parameters to vary and how to vary them. In general, economics will dictate the selection of process parameters.

In some embodiments, one or more of the following parameters are varied: type of feed material, composition of feed material, amount of oxygen, location(s) in which oxygen is added, amount of steam, location(s) in which steam is added, ratio of oxygen to steam, temperature profile, pressure profile, type of catalyst, composition of catalyst, catalyst concentration profile, location(s) in which catalyst is added, catalyst activity, average residence time, and residence-time distribution. Initial values or ranges for any of these input parameters can be selected based on the values described herein.

In some embodiments, the variation in one or more of these parameters improves one or more of the following: yield of the syngas; rate of conversion to the syngas; ratio of $H_2/CO$ in the syngas at one or more points; average and/or dynamic concentration profiles of $CO$, $H_2$, $O_2$, $CO_2$, $H_2O$; output catalyst composition; overall and/or unit-specific energy balance; overall and/or unit-specific mass balance; economic output; yield of one or more products from syngas, such as $C_2$-$C_4$ alcohols (e.g., more particularly, ethanol); product selectivity; or rate of production of one or more desired compounds.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent that there are variations of the invention, which are within the spirit of the disclosure or equivalent to the inventions found in the appended claims, it is the intent that this patent will cover those variations as well. The present invention shall only be limited by what is claimed.

What is claimed is:

1. A method of forming a product, said method comprising the steps of:
   (a) devolatilizing a carbon-containing feed material to form a gas phase and a solid phase in a devolatilization unit;
   (b) passing said gas phase and said solid phase through a heated reaction vessel to form syngas;
   (c) converting said syngas to a product,
   wherein step (a) is performed in the presence of free oxygen in an amount between about 0.1% and about 25% of the stoichiometric amount of oxygen to completely combust said feed material; and
   wherein said product is selected from $C_2$ to $C_4$ alcohols.

2. The method of claim 1, wherein said product is ethanol.
3. The method of claim 1, wherein said product is propanol.
4. The method of claim 1, wherein said product is butanol.

5. The method of claim 1, wherein step (b) is performed in the presence of free oxygen in an amount between about 0.1% and about 50% of the stoichiometric amount of oxygen to completely combust the carbon contained in said solid phase produced in step (a).

6. The method of claim 1, wherein said amount of free oxygen is less than about 10% of the stoichiometric amount of oxygen to completely combust said feed material.

7. The method of claim 6, wherein said amount of free oxygen is less than about 1% of the stoichiometric amount of oxygen to completely combust said feed material.

8. The method of claim 7, wherein said amount of free oxygen is less than about 0.5% of the stoichiometric amount of oxygen to completely combust said feed material.

9. The method of claim 1, wherein said amount of free oxygen is greater than about 1% of the stoichiometric amount of oxygen to completely combust said feed material.

10. The method of claim 1, wherein step (a) is further performed in the presence of added steam.

11. The method of claim 10, wherein said added steam is present in an amount that is less than about 50% of the stoichiometric amount of water to completely convert said feed material to carbon monoxide and hydrogen.

12. The method of claim 11, wherein said added steam is present in an amount that is less than about 10% of the stoichiometric amount of water to completely convert said feed material to carbon monoxide and hydrogen.

13. The method of claim 10, wherein a first amount of steam is present from initial moisture in said carbon-containing feed material, a second amount of steam is added during step (a), and the combined first amount and second amount of steam is less than the stoichiometric amount of water to completely convert said feed material to carbon monoxide and hydrogen.

14. The method of claim 10, wherein a first amount of steam is present from initial moisture in said carbon-containing feed material, a second amount of steam is added during step (a), and the combined first amount and second amount of steam is greater than the stoichiometric amount of water to completely convert said feed material to carbon monoxide and hydrogen.

15. A method of forming a product, said method comprising the steps of:
   (a) devolatilizing a carbon-containing feed material to form a gas phase and a solid phase in a devolatilization unit;
   (b) passing said gas phase and said solid phase through a heated reaction vessel to form syngas;
   (c) converting said syngas to a product,
   wherein step (b) is performed in the presence of free oxygen in an amount between about 0.1% and about 50% of the stoichiometric amount of oxygen to completely combust the carbon contained in said solid phase produced in step (a); and
   wherein said product is selected from $C_2$ to $C_4$ alcohols.

16. The method of claim 15, wherein said amount of free oxygen is less than about 25% of the stoichiometric amount of oxygen to completely combust the carbon contained in said solid phase produced in step (a).

17. The method of claim 16, wherein said amount of free oxygen is less than about 10% of the stoichiometric amount of oxygen to completely combust the carbon contained in said solid phase produced in step (a).

18. The method of claim 15, wherein step (b) is performed in the presence of steam.

19. The method of claim 18, wherein an initial ratio of free oxygen to steam ($O_2/H_2O$) in step (b) is less than about 1.

20. The method of claim 19, wherein said initial ratio $O_2/H_2O$ is less than about 0.5.

21. The method of claim 20, wherein said initial ratio $O_2/H_2O$ is between about 0.01 and about 0.2.

22. The method of claim 1 or 15, further comprising the substeps of (i) measuring the composition of said gas phase and/or said solid phase, (ii) determining a suitable amount of free oxygen based on predicted partial oxidation of at least some of said composition to syngas, and (iii) introducing a gas containing said suitable amount of free oxygen.

23. The method of claim 1 or 15, wherein said gas phase is removed, at least in part, during step (a).

24. The method of claim 23, wherein prior to step (b), said solid phase is combined with gas removed during step (a).

25. The method of claim 1 or 15, wherein said devolatilization unit is a multiple-stage unit in which both said gas phase and said solid phase pass through at least one stage of said devolatilization unit and at least a portion of said gas phase is removed from said devolatilization unit prior to a final stage.

26. The method of claim 25, wherein different amounts of oxygen are added across stages of said devolatilization unit.

27. The method of claim 25, wherein oxygen is added to said devolatilization unit prior to removal of at least a portion of said gas phase.

28. The method of claim 25, wherein after at least a portion of said gas phase is removed, oxygen is added to said devolatilization unit.

29. The method of claim 25, wherein a first amount of oxygen is added prior to removal of at least a portion of said gas phase, and wherein a second amount of oxygen is added after removal of at least a portion of said gas phase.

30. The method of claim 29, wherein said first amount of oxygen is greater than said second amount of oxygen.

31. The method of claim 1 or 15, wherein the presence of free oxygen decreases the ratio of hydrogen to carbon monoxide in said syngas, compared to the ratio of hydrogen to carbon monoxide produced by the same method in the absence of oxygen.

32. The method of claim 1 or 15, wherein the presence of free oxygen increases the amount of product produced compared to the amount of product produced by the same method in the absence of free oxygen.

33. The method of claim 1 or 15, further comprising introducing at least some of a stream produced in one or more steps selected from the group consisting of step (a), step (b), and step (c) to a reactor configured with an input for a gas comprising oxygen, wherein at least some of said stream is partially oxidized to produce additional syngas.

34. The method of claim 1 or 15, wherein step (c) comprises the substeps of:
  (i) introducing a first amount of syngas into a first reaction zone comprising at least a first catalyst;
  (ii) converting at least a portion of said first amount of syngas to methanol with said first catalyst;
  (iii) introducing said methanol to a second reaction zone comprising at least a second catalyst;
  (iv) introducing a second amount of syngas to said second reaction zone; and
  (iv) reacting at least a portion of said methanol introduced into said second reaction zone with at least a portion of said second amount of syngas with said second catalyst to produce a product stream comprising ethanol.

35. The method of claim 34, wherein said second amount of syngas includes syngas that did not react in said first reaction zone.

36. The method of claim 34, wherein said second amount of syngas includes syngas that was separated and recycled from said product stream.

37. The method of claim 34, wherein said first catalyst comprises a material selected from the group consisting of $ZnO/Cr_2O_3$, $Cu/ZnO$, $Cu/ZnO/Al_2O_3$, $Cu/ZnO/Cr_2O_3$, $Cu/ThO_2$, Co/S, Mo/S, Co/Mo/S, Ni/S, Ni/Mo/S, Ni/Co/Mo/S, and any of the foregoing in combination with Mn and/or V, and wherein said first catalyst optionally includes a basic promoter.

38. The method of claim 34, wherein said second catalyst comprises a material selected from the group consisting of $ZnO/Cr_2O_3$, $Cu/ZnO$, $Cu/ZnO/Al_2O_3$, $CuO/CoO$, $CuO/CoO/Al_2O_3$, Co/S, Mo/S, Co/Mo/S, $Rh/Ti/SiO_2$, $Rh/Mn/SiO_2$, $Rh/Ti/Fe/Ir/SiO_2$, Rh/Mn/MCM-41, Ni/S, Ni/Mo/S, Ni/Co/Mo/S, and any of the foregoing in combination with Mn and/or V, and wherein said second catalyst optionally includes a basic promoter.

39. The method of claim 34, wherein said first and second catalysts have substantially the same composition.

40. The method of claim 34, wherein said first reaction zone is in a first reactor, said second reaction zone is in a second reactor, and an output stream of said first reactor comprises syngas introduced from said first reaction zone into said second reaction zone, further comprising separating from said output stream at least a portion of said methanol produced in said first reaction zone.

41. The method of claim 34, wherein said first reaction zone and second reaction zone are both in a single reactor.

42. The method of claim 34, wherein either of said reaction zones comprises at least two reactors.

43. The method of claim 34, further comprising introducing additional or recycled $CO_2$ into said first reaction zone, wherein at least a portion of said $CO_2$ is reacted with $H_2$ present to produce $CO_2$-derived methanol.

44. The method of claim 43, wherein said $CO_2$ was produced during step (a) and/or step (b) and recycled into said first reaction zone.

45. The method of claim 15, wherein said product is ethanol.

46. The method of claim 15, wherein said product is butanol.

47. A method of forming a product, said method comprising the steps of:
  (a) devolatilizing a carbon-containing feed material to form a gas phase and a solid phase in a devolatilization unit, wherein said gas phase comprises syngas; and
  (b) converting said syngas to a product,
  wherein step (a) is performed in the presence of free oxygen in an amount between about 0.1% and about 25% of the stoichiometric amount of oxygen to completely combust said feed material; and
  wherein said product is selected from $C_2$ to $C_4$ alcohols.

48. The method of claim 47, wherein said product is ethanol.

49. The method of claim 47, wherein said product is propanol.

50. The method of claim 47, wherein said product is butanol.

* * * * *